United States Patent
Wong et al.

(10) Patent No.: US 10,005,847 B2
(45) Date of Patent: *Jun. 26, 2018

(54) ANTI-HER2 GLYCOANTIBODIES AND USES THEREOF

(71) Applicant: Academia Sinica, Taipei (TW)

(72) Inventors: Chi-Huey Wong, Rancho Santa Fe, CA (US); Chung-Yi Wu, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/723,181

(22) Filed: May 27, 2015

(65) Prior Publication Data

US 2015/0344587 A1 Dec. 3, 2015

Related U.S. Application Data

(60) Provisional application No. 62/003,104, filed on May 27, 2014, provisional application No. 62/020,199, filed on Jul. 2, 2014, provisional application No. 62/110,338, filed on Jan. 30, 2015.

(51) Int. Cl.
| | |
|---|---|
| C07K 16/32 | (2006.01) |
| C07K 16/40 | (2006.01) |
| A61K 31/517 | (2006.01) |
| A61K 39/395 | (2006.01) |
| C07K 16/28 | (2006.01) |
| C12P 21/00 | (2006.01) |

(52) U.S. Cl.
CPC ............ *C07K 16/40* (2013.01); *A61K 31/517* (2013.01); *A61K 39/3955* (2013.01); *C07K 16/283* (2013.01); *C07K 16/32* (2013.01); *C12P 21/005* (2013.01); *C12Y 302/01* (2013.01); *C12Y 302/01051* (2013.01); *C07K 2317/14* (2013.01); *C07K 2317/24* (2013.01); *C07K 2317/31* (2013.01); *C07K 2317/40* (2013.01); *C07K 2317/41* (2013.01); *C07K 2317/732* (2013.01); *C07K 2317/92* (2013.01)

(58) Field of Classification Search
CPC .... C12P 21/005; C07K 16/32; C12Y 2317/41
USPC .......................... 424/133.1, 158.1; 530/389.1
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |

(Continued)

FOREIGN PATENT DOCUMENTS

| | | |
|---|---|---|
| EP | 404097 A2 | 12/1990 |
| EP | 0341735 B1 | 9/1992 |

(Continued)

OTHER PUBLICATIONS

Wright et al (Springer Semin Immunopathology ,15 :259-273 (1993)).*
Olden et al (Biochem et Biophys Acta 650:209-232 (1982)).*
Delente (Trends in Biotechnology 3, letters to editor, No. 9, (1985)).*
Li et al. Analytica Chimica Acta 924 (2016) 77-85.*
Lin et al. PNAS (Aug. 25, 2015) vol. 112( No. 34): 10611-10616.*
Ahmed et al. J. Mol. Biol. (2014) 426, 3166-3179.*
Abrahmsén et al, "Analysis of signals for secretion in the staphylococcal protein A gene," *EMBO J.*, Dec. 30, 1985, 4(13B):3901-3906.
Altschul SF et al., "Basic local alignment search tool", *J Mol Biol.* Oct. 5, 1990;215(3):403-10.
Altschul SF, et al., "Gapped BLAST and PSI-BLAST: a new generation of protein database search programs", *Nucleic Acids Res.* Sep. 1, 1997;25(17):3389-402.
Anderson et al., "Stimulation of Natural Killer T Cells by Glycolipids", *Molecules*, May 2013, 18(12), 15662-15688.
Arié et al., "Chaperone function of FkpA, a heat shock prolyl isomerase, in the periplasm of *Escherichia coli*," *Mol. Microbiol.*, Jan. 2001, 39(1):199-210.
Bachmann, *Cellular and Molecular Biology*, vol. 2, Chapter 72: *Derivations and Genotypes of Some Mutant Derivatives of Escherichia coli K-12*, Neidhardt et al., eds., 1987, pp. 1190-1219, American Society for Microbiology, Washington, D.C.

(Continued)

*Primary Examiner* — Lynn A Bristol
(74) *Attorney, Agent, or Firm* — Duane Morris LLP

(57) ABSTRACT

The present disclosure relates to a novel class of anti-HER2 monoclonal antibodies comprising a homogeneous population of anti-HER2 IgG molecules having the same N-glycan on each of Fc. The antibodies of the invention can be produced from anti-HER2 monoclonal antibodies by Fc glycoengineering. Importantly, the antibodies of the invention have improved therapeutic values with increased ADCC activity and increased Fc receptor binding affinity compared to the corresponding monoclonal antibodies that have not been glycoengineered.

11 Claims, 7 Drawing Sheets

(56) References Cited

U.S. PATENT DOCUMENTS

| | | |
|---|---|---|
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Carter et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |

(56) References Cited

U.S. PATENT DOCUMENTS

| | | |
|---|---|---|
| 9,221,859 B2 | 12/2015 | Withers |
| 9,382,284 B2 | 7/2016 | Withers |
| 9,434,786 B2 | 9/2016 | Wang |
| 9,803,177 B2 | 10/2017 | Rossi et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1 | 3/2015 | Wang |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1* | 12/2015 | Wong .................. C12N 9/24 424/133.1 |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaheen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |

(56) References Cited

FOREIGN PATENT DOCUMENTS

| | | |
|---|---|---|
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |
| WO | WO 2014/031762 A1 | 2/2017 |

OTHER PUBLICATIONS

Baldwin et al., "Monoclonal antibodies in cancer treatment," Lancet, Mar. 15, 1986, 327(8481):603-605.

Barbas et al., "Assembly of combinatorial antibody libraries on phage surfaces: the gene III site," Proc. Natl. Acad. Sci. U.S.A., Sep. 15, 1991, 88(18):7978-7982.

Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.

Barbas et al., "Semisynthetic combinatorial antibody libraries: a chemical solution to the diversity problem," Proc. Natl. Acad. Sci. U.S.A., May 15, 1992, 89(10):4457-4461.

Barnes et al., "Methods for growth of cultured cells in serum-five medium," Anal. Biochem., Mar. 1, 1980, 102(2):255-270.

Baselga J, et al., "Phase II study of weekly intravenous recombinant humanized anti-p185HER2 monoclonal antibody in patients with HER2/neu-overexpressing metastatic breast cancer", J Clin Oncol. Mar. 1996;14(3):737-44.

Bass et al., "Hormone phage: an enrichment method for variant proteins with altered binding properties," Proteins, 1990, 8(4):309-314.

Beck A., "Biosimilar, biobetter and next generation therapeutic antibodies" MAbs. Mar.-Apr. 2011;3(2):107-10. Epub Mar. 1, 2011.

Berra et al., "Correlation between ganglioside distribution and histological grading of human astrocytomas," Int. J. Cancer, Sep. 15, 1985, 36(3):363-366.

Birklé et al., "Role of tumor-associated gangliosides in cancer progression," Biochimie, Mar.-Apr. 2003, 85(3-4):455-463.

Bobo et al., "Convection-enhanced delivery of macromolecules in the brain," Proc. Natl. Acad. Sci. U.S.A., Mar. 15, 1994, 91(6) 2076-2080.

Boerner et al., "Production of antigen-specific human monoclonal antibodies from in vitro-primed human splenocytes," J. Immunol., Jul. 1, 1991, 147(1):86-95.

Bothmann et al., "The periplasmic Escherichia coli peptidylprolyl cis,trans-isomerase FkpA. I. Increased functional expression of antibody fragments with and without cis-prolines," J. Biol. Chem., Jun. 2, 2000, 275(22):17100-17105.

Brennan et al., "Preparation of bispecific antibodies by chemical recombination of monoclonal immunoglobulin $G_1$ fragments," Science, Jul. 5, 1985, 229(4708):81-83.

Brimble et al., "The cell surface glycosphingolipids SSEA-3 and SSEA-4 are not essential for human ESC pluripotency," Stem Cells, Jan. 2007, 25(1):54-62.

Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.

Brüggemann et al., "Designer mice: the production of human antibody repertoires in transgenic animals," Year in Immunol., 1993, 7:33-40.

Capel PJ et al., "Heterogeneity of human IgG Fc receptors" Immunomethods. Feb. 1994;4(1):25-34.

Carter et al., "High level Escherichia coli expression and production of a bivalent humanized antibody fragment," Nature Biotechnology, Feb. 1992, 10(2):163-167.

Carter et al., "Humanization of an anti-p185$^{HER2}$ antibody for human cancer therapy," Proc. Natl. Acad. Sci. U.S.A., May 15, 1992, 89(10):4285-4289.

Carter PJ. "Potent antibody therapeutics by design" Nat Rev Immunol. May 2006;6(5):343-357.

Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.

Chen et al., "Chaperone activity of DsbC," J. Bio. Chem., Jul. 9. 1999, 274(28):19601-19605.

Chen et al., "Selection and analysis of an optimized anti-VEGF antibody: crystal structure of an affinity-matured Fab in complex with antigen," J. Mol. Biol., Nov. 5, 1999, 293(4):865-881.

Chen et al., "Selective killing of transformed cells by cyclin/cyclin-dependent kinase 2 antagonists," Proc. Natl. Acad. Sci. U.S.A., Apr. 13, 1999, 96(8):4325-4329.

Chothia et al., "Canonical structures for the hypervariable regions of immunoglobulins," J. Mol. Biol., Aug. 20, 1987, 196(4):901-917.

Clackson et al., "Making antibody fragments using phage display libraries," Nature, Aug. 15, 1991, 352(6336):624-628.

Clark EA et al., "Structure, function, and genetics of human B cell-associated surface molecules" Adv Cancer Res. 1989;52:81-149.

Clynes R, et al., "Fc receptors are required in passive and active immunity to melanoma" Proc Natl Acad Sci U S A. Jan. 20, 1998;95(2):652-6.

Cunningham et al., "High-resolution epitope mapping of hGH-receptor interactions by alanine-scanning mutagenesis," Science, Jun. 2, 1989, 244(4908):1081-1085.

(56) References Cited

OTHER PUBLICATIONS

Daëron, "Fc receptor biology," *Annu. Rev. Immunol.*, 1997, 15:203-234.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGκ monoclonal antibodies from a novel strain of minilocus transgenic mice," *Nature Biotechnol.*, Jul. 1996, 14(7):845-851.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential anglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Galfré et al., "Preparation of monoclonal antibodies: strategies and procedures," *Methods Enzymol.*, 1981, 73(Pt B):3-46.
Gazzano-Santoro et al., "A non-radioactive complement-dependent cytotoxicity assay for anti-CD20 nonclonal antibody," *J. Immunol. Methods*, Mar. 28, 1997, 202(2):163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice* 2$^{nd}$ed., Chapter 3: Production of Monoclonal Antibodies, 1986, pp. 59-103, Academic Press, London.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gottschling et al., "Stage-specific embryonic antigen-4 is expressed in basaloid lung cancer and associated with poor prognosis," *Eur. Respir. J.*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in Escherichia coli," *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of Escherichia coli," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hata, K. et al., "Limited Inhibitory Effects of Oseltamivir and Zanamivir on Human Sialidases," Antimicrobial Agents and Chemotherapy, vol. 52, No. 10, Oct. 2008, in 8 pages.
Hawkins et al., "Selection of phage antibodies by binding affinity. Mimicking affinity maturation," *J. Mol. Biol.*, 1992, 226(3):889-896.
Heyman, "Complement and Fc-receptors in regulation of the antibody response," *Immunol. Lett.*, Dec. 1996, 54(2-3):195-199.
Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Honegger et al., "Yet another numbering scheme for immunoglobulin variable domains. an automatic modeling and analysis tool," *J. Mol. Biol.*, Jun. 8, 2001, 309:657-670.
Hoogenboom et al., "By-passing immunisation. Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of F(ab')$_{2\mu}$fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.

(56) References Cited

OTHER PUBLICATIONS

Jenkins N, Curling EM., "Glycosylation of recombinant proteins: problems and prospects", *Enzyme Microb Technol.* May 1994;16(5):354-64.

Jones et al., "Rapid PCR-cloning of full-length mouse immunoglobulin variable regions," *Nature Biotechnol.*, Jan. 1991, 9(1):88-89.

Jones et al., "Replacing the complementarity-determining regions in a human antibody with those from a mouse," *Nature*, May 29-Jun. 4, 1986, 321(6069):522-525.

Jones, "Analysis of polypeptides and proteins," *Adv. Drug Delivery Rev.*, Jan.-Apr. 1993, 10(1):29-90.

Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.

Kaneko et al., "Anti-inflammatory activity of immunoglobulin G resulting from Fc sialylation," *Science*, Aug. 4, 2006, 313(5787):670-673.

Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.

Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.

Karlin S. et al., "Methods for assessing the statistical significance of molecular sequence features by using general scoring schemes", *Proc Natl Acad Sci U S A*. Mar. 1990;87(6):2264-8.

Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.

Kim et al., "Localization of the site of the murine IgG1 molecule that is involved in binding to the murine intestinal Fc receptor," *Eur. J. Immunol.*, 1994, 24:2429-2434.

Köhler et al., "Continuous cultures of fused cells secreting antibody of predefined specificity," *Nature*, Aug. 7, 1975, 256(5517):495-497.

Kontermann, "Intrabodies as therapeutic agents," *Methods*, Oct. 2004, 34(2):163-170.

Kostelny et al., "Formation of a bispecific antibody by the use of leucine zippers," *J. Immunol.*, Mar. 1, 1992, 148(5):1547-1553.

Kozbor, "A human hybrid myeloma for production of human monoclonal antibodies," *J. Immunol.*, Dec. 1984, 133(6):3001-3005.

Kriegler M et al., "A novel form of NF/cachectin is a cell surface cytotoxic transmembrane protein: ramifications for the complex physiology of TNF" *Cell.* Apr. 8, 1988;53(1):45-53.

Kudo et al., "Up-regulation of a set of glycosyltransferase genes in human colorectal cancer," *Lab. Invest.*, Jul. 1998, 78(7):797-811.

Lau et al., "N-Glycans in cancer progression," *Glycobiology*, Oct. 2008, 18(10):750-760.

Lee et al., "Bivalent antibody phage display mimics natural immunoglobulin," *J. Immunol. Methods*, Jan. 2004, 284(1-2):119-132.

Lee et al., "High-affinity human antibodies from phage-displayed synthetic Fab libraries with a single framework scaffold," *J. Mol. Biol.*, Jul. 23, 2004, 340(5):1073-1093.

Lefranc et al., "IMGT, the international ImMunoGeneTics database," *Nucleic Acids Res.*, Jan. 1, 1999, 27(1):209-212.

Lehninger, *Biochemistry: The Molecular Basis of Cell Structure and Function*, 2nd ed., 1975, pp. 73-75, Worth Publishers, New York.

Leung et al., "A method for random mutagenesis of a defined DNA segment using a modified polymerase chain reaction," *Technique—A Journal of Methods in Cell and Molecular Biology*, Aug. 1989, 1(1):11-15.

Lindmark et al., "Binding of immunoglobulins to protein A and immunoglobulin levels in mammalian sera," *J. Immunol. Meth.*, Aug. 12, 1983, 62(1):1-13.

Liu C, et al., "Expansion of spleen myeloid suppressor cells represses NK cell cytotoxicity in tumor-bearing host" *Blood.* May 15, 2007;109(10):4336-42. Epub Jan. 23, 2007.

Liu et al., "Eradication of large colon tumor xenografts by targeted delivery of maytansinoids," *Proc. Natl., Acad. Sci. U.S.A.*, Aug. 6, 1996, 93(16):8618-8623.

LoBuglio et al., "Mouse/human chimeric monoclonal antibody in man: kinetics and.immune response," *Proc. Natl. Acad. Sci. U.S.A.*, Jun. 1989, 86(11):4220-4224.

Lode et al., "Targeted therapy with a novel enediyene antibiotic calicheamicin $\Theta^I_1$ effectively suppresses growth and dissemination of liver metastases in a syngeneic model of murine neuroblastoma," *Cancer Res.*, Jul. 15, 1998, 58(14):2925-2928.

Lonberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Louis et al., "The 2007 WHO classification of tumours of the central nervous system," *Acta. Neuropathol.*, Aug. 2007, 114(2):97-109.

Lu et al., "Single chain anti-c-Met antibody conjugated nanoparticles for in vivo tumor-targeted imaging and drug delivery," *Biomaterials*, Apr. 2011, 32(12):3265-3274.

MacFarlane GT, et al., "Formation of glycoprotein degrading enzymes by Bacteroides fragilis" *FEMS Microbiol Lett.* Jan. 15, 1991;61(2-3):289-93.

Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

Mandler et al., "Modifications in synthesis strategy improve the yield and efficacy of geldanamycin-herceptin immunoconjugates," *Bioconjugate Chem.*, Jul.-Aug. 2002, 13(4):786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marks et al., "By-passing immunization Human antibodies from V-gene libraries displayed on phage," *J. Mol. Biol.*, Dec. 5, 1991, 222(3):581-597.

Marks et al., "By-passing immunization: Building high affinity human antibodies by chain shuffling," *Nature Biotechnology*, Jul. 1992, 10(7):779-783.

Mather et al., "Culture of testicular cells in hormone-supplemented serum-five medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matsuda et al.,"Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

McKimm-Breschkin, J. et al. "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Meyer, "Malignant gliomas in adults," *N. Engl. J. Med.*, Oct. 23, 2008, 359(17):1850.

(56) References Cited

OTHER PUBLICATIONS

Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Morelle, W. et al., "The Mass Spectrometric Analysis of Glycoproteins and their Glycan Stuctures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology.* Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Munson et al., "Ligand: a versatile computerized approach for characterization of ligand-binding systems," *Anal. Biochem.*, Sep. 1, 1980, 107(1):220-239.
Neuberger et al.,"Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Noto et al., "CD44 and SSEA-4 positive cells in an oral cancer cell line HSC-4 possess cancer stem-like cell characteristics," *Oral Oncol.*, Aug. 2013, 49(8):787-795.
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Papanastassiou et al., "The potential for efficacy of the modified (ICP 34.5 ) herpes simplex virus HSV1716 following intratumoural injection into human malignant glioma: a proof of principle study," *Gene Therapy*, Mar. 2002, 9(6):398-406.
Pearlman et al., *Peptide and Protein Drug Delivery, Chapter 6: Analysis of Protein Drugs*, Lee, ed., 1991, pp. 247-301, Marcel Dekker Publishing, New York.
Peipp et al., "Antibody fucosylation differentially impacts cytotoxicity mediated by NK and PMN effector cells," *Blood*, 2008, 112(6):2390-2399.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.

Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Proba et al., "Functional antibody single-chain fragments from the cytoplasm of *Escherichia coli*: influence of thioredoxin reductase (TrxB)," *Gene*, Jul. 4, 1995, 159(2):203-207.
Puigò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Roguska et al., "Humanization of murine monoclonal antibodies through variable domain resurfacing," *Proc. Natl. Acad. Sci. U.S.A.*, Feb. 1, 1994, 91(3):969-973.
Roos et al., "Specific inhibition of the classical complement pathway by C1q-binding peptides," *J. Immunol.*, Dec. 15, 2001, 167(12):7052-7059.
Rowland et al, "Drug localisation and growth inhibition studies of vindesine-monoclonal anti-CEA conjugates in a human tumour xenograft," *Cancer Immunol Immunother.*, 1986, 21(3):183-187.
Ruiz et al., "IMGT, the international ImMunoGeneTics database," *Nucl. Acids Res.*, Jan. 1, 2000, 28(1):219-221.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.

(56) References Cited

OTHER PUBLICATIONS

Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.
Slamon DJ, et al., "Human breast cancer: correlation of relapse and survival with amplification of the HER-2/neu oncogene" *Science*. Jan. 9, 1987; 235(4785):177-82.
Smith RA et al., "The active form of tumor necrosis factor is a trimer" *J Biol Chem*. May 25, 1987;262(15):6951-4.
Smyth MJ, et al., "CD4+CD25+ T regulatory cells suppress NK cell-mediated immunotherapy of cancer" *J Immunol*. Feb. 1, 2006;176(3):1582-7.
Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res*. Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2): 109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Tsai TI, et al., "Effective sugar nucleotide regeneration for the large-scale enzymatic synthesis of Globo H and SSEA4" *J Am Chem Soc*. Oct. 2, 2013;135(39):14831-9, Epub Sep. 17, 2013.
Tutt et al., "Trispecific F(ab')$_3$ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology*. Jan. 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem*. Jul. 5, 1989;264(19):11282-7.
van Beek et al., "Increased sialic acid density in surface glycoprotein of transformed and malignant cells—a general phenomenon?" *Cancer Res.*, Nov. 1973, 33(11):2913-2922.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J*. Jan. 2000;78(1):394-404.
Wang et al., "Glycan microarray of Globo H and related structures for quantitative analysis of breast cancer," *Proc. Natl. Acad. Sci. U.S.A.*, Aug. 19, 2008, 105(33):11661-11666.
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Wikstrand et al., "Monoclonal antibody therapy of human gliomas: Current status and future approaches," *Cancer Metastasis Rev.*, 1999, 18(4):451-464.
Williams et al., "Cloning and sequencing of human immunoglobulin V lambda gene segments." *Eur. J. Immunol.*, Jul. 1993, 23(7):1456-1461.
Winter et al., "Making antibodies by phage display technology," *Annu. Rev. Immunol.*, 1994, 12:433-455.
Woof et al., "Human antibody-Fc receptor interactions illuminated by crystal structures," *Nat. Rev. Immunol.*, Feb. 2004, 4(2):89-99.
Yansura et al., "Nucleotide sequence selection for increased expression of heterologous genes in *Escherichia coli*," *Methods: A Companion to Methods in Enzymol.*, Aug. 1992, 4(2):151-158.
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yu et al., "Anti-GD2 antibody with GM-CSF, interleukin-2, and isotretinoin for neuroblastoma," *N. Engl. J. Med.*, Sep. 30, 2010, 363(14):1324-1334.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "Selection of tumor antigens as targets for immune attack using immunohistochemistry: I. Focus on gangliosides," *Int. J. Cancer*, Sep. 26, 1997, 73(1):42-49.
European Search Report issued in connection with corresponding European Patent Application No. 15181446.4, dated Dec. 7, 2015, 10 pages.
International Search Report and Written Opinion issued for International application No. PCT/US2015/032738, dated Oct. 20, 2015, 15 pages.
International Search Report and Written Opinion issued for International application No. PCT/US2015/032744, dated Oct. 2, 2015, 12 pages.
International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, dated Dec. 14, 2015, 3 pages.

(56) References Cited

OTHER PUBLICATIONS

U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.
Abbas et al., "Functional diversity of helper T lymphocytes," Nature, Oct. 31, 1996, 383(6603):787-793.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," Nat. Biotechnol., Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Altevogt, Peter et al., Different Patterns of Lectin Binding and Cell Surface Sialylation Detected on Related High- and Low-Metastatic Tumor Lines, Cancer Res. 43, 5138-5144, 1983.
Amin, M. N. et al. Synthetic glycopeptides reveal the glycan specificity of HIV-neutralizing antibodies. Nat. Chem. Biol. 9, 521-526, (2013.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," Chem. Rev., Feb. 2002, 102(2):439-469.
Anthony, Robert et al., Recapitulation of IVIG Anti-Inflammatory Activity with a Recombinant lgG Fc, Science Apr. 18, 2008. 320:373-376.
Arase et al., "NK1.1$^+$ CD4$^+$ CD8$^-$ thymocytes with specific lymphokine secretion," Eur. J. Immunol., Jan. 1993, 23(1):307-310.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," Nature, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barouch, D. H. Challenges in the development of an HIV-I vaccine. Nature 455, 613-619, (2008).
Barry, C.S. et al., 'Naked' and Hydrated Conformers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R. "In vivo imaging of membraneassociated glycans in developing zebrafish." Science 2008, 320, 664-667.

Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," Glycobiology, Feb. 2010, 20(2):148-157.
Blixt, O. et al. Printed covalent glycan array for ligand profiling of diverse glycan binding proteins. Proc. Natl. Acad. Sci. U.S. A. 101, 17033-17038, (2004.
Boens, N. et al., "Fluorescent indicators based on BODIPY." Chem. Soc. Rev. 2012, 41, 1130-1172.
Borg et al., "CD1d-lipid-antigen recognition by the semi-invariant NKT T-cell receptor," Nature, Jul. 5, 2007, 448(7149):44-49.
Bosmann et al., "Enzyme activity in invasive tumors of human breast and colon," Proc. Natl. Acad. Sci. USA, May 1974, 71(5):1833-1837.
Bost, Kenneth et al., Antibodies Against A Peptide Sequence Within The HIV Envelope Protein Crossreacts With Human Interleukin-2, Immunol. Invest., 17: 577-586 (1988).
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Bricard et al., "Enrichment of human CD4$^+$ Vα24/Vβ11 invariant NKT cells in intrahepatic malignant tumors," J. Immunol., Apr. 15, 2009, 182(2):5140-5151.
Bruchez, Marcel et al. Semiconductor Nanocrystals as Fluorescent Biological Labels, Science 281:2013-2016, 1998.
Buchini et al., "Towards a new generation of specific Trypanosoma cruzi trans-sialidase inhibitors," Angew. Chem. Int. Ed. Engl., 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Carlsson, Jan et al., Protein Thiolation and Reversible Protein-Protein Conjugation, Biochem J 173: 723-737 (1978).
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" MMWR, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).

(56) References Cited

OTHER PUBLICATIONS

Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," *Proc. Natl. Acad. Sci. USA*, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjuates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Cheng, Peter et al., Oseltamivir- and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3Ga1T5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Domain association in immunoglobulin molecules. The packing of variable domains," *J. Mol. Biol.*, Dec. 5, 1985, 186(3):651-663.
Codelli, J. A. et al., Second-Generation Difluorinated Cyclooctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2.6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.
Cyranoski, Threat of Pandemic Brings Flu Drug Back to Life, Nat. Med. Sep. 2005, 11(9): 909.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine αβ T cells expressing invariant TCR alpha-chains," *J. Immunol.*, Jun. 15, 1997, 158(12):5603-5611.
de Almeida et al., "Thiacycloalkynes for copper-free click chemistry," *Angew. Chem. Int. Ed. Engl.*, Mar. 5, 2012, 51(10):2443-2447.
Debets, M. F. et al., Bioconjugation with Strained Alkenes and Alkynes, Acc. Chem. Res. 2011, 44, 805-815.
Dejong et al., Fatal outcome of human influenza A (H5N1) is associated with high viral load and hypercytokinemia. Nat Med Oct. 2006;12(10):1203-7. Epub Sep. 10, 2006.
Dellabona et al., "An invariant Vα24-JαQ/Vβ11 T cell receptor is expressed in all individuals by clonally expanded CD4−8−T cells," *J. Exp. Med.*, Sep. 1, 1994, 180(3):1171-1176.
Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "α-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," *J. Exp. Med.*, Jun. 16, 2003, 197(12):1667-1676.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Eberl et al., "Selective bystander proliferation of memory CD4+ and CD8+ T cells upon NK T or T cell activation," *J. Immunol.*, Oct. 15, 2000, 165(8):4305-4311.

(56) References Cited

OTHER PUBLICATIONS

Eberl et al., "Selective induction of NK cell proliferation and cytotoxicity by activated NKT cells," Eur. J. Immunol., Apr. 2000, 30(4):985-992.

Eggink, D. et al. Lack of complex N-glycans on HIV-I envelope glycoproteins preserves protein conformation and entry function. Virology 401, 236-247, (2010).

Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.

Ellis J., et al., Evaluation of Four Real-Time PCR Assays for Detection of Influenza A9H1N1)v Viruses, Euro Surveill. 2009; 14(22), p. 1-3.

Evans, Michael et al., "Mechanism-based profiling of enzyme families," Chem. Rev., Aug. 2006, 106(8):3279-3301.

Evans, "The rise of azide-alkyne 1,3-dipolar 'click' cycloaddition and its application to polymer science and surface modification," Australian J. Chem., Jun. 2007, 60(6):384-395.

Extended European Search Report dated Jan. 5, 2016 in European Patent Application No. 13830785.5, in 10 pages.

Falkowska, E. et al. Broadly neutralizing HIV antibodies define a glycan-dependent epitope on the prelusion conformation of gp41 on cleaved envelope trimers. Immunity 40, 657-68, 2014.

Fan, Shu-Quan et al., Remarkable Transglycosylation Activity of Glycosynthase Mutants of Endo-D, an Endo-β-N-acetylglucosaminidase from Streptococcus pneumoniae, JBC vol. 287, No. 14, pp. 11272-11281, Mar. 30, 2012.

Fazio, F. et al., Synthesis of sugar arrays in microtiter plate. J. Am. Chem. Soc. 124, 14397-14402, (2002).

FDA Guidance for Industry for Container Closure Systems for Packaging Human Drugs and Biologics, May 1999.

Fedson, Confronting the next influenza pandemic with anti-inflammatory and immunomodulatory agents: why they are needed and how they might work. Influenza Other Respi Virusts. Jul. 2009;3(4):129-42.

Feizi, Ten, Carbohydrate Differentiation Antigens: Probable Ligands for Cell Adhesion Molecules,Trends Biochem. Sci. 16, 84-86.

Fernandez-Tejada, Alberto et al., Designing synthetic vaccines for HIV. Expert Rev. Vaccines 14, 815-31, 2015.

Fernandez-Megia et al., A Click Approach to Unprotected Glycodendrimers. Macromolecules 2006, vol. 39, pp. 2113-2120.

Fessner et al., Enzymes in Organic Synthesis, Short Enzymatic Synthesis of L-Fucose Analogs. Eur. J. Org. Chem 2000, p. 125-132.

Fiehn, Oliver, Combining Genomics, Metabolome Analysis, and Biochemical Modelling to Understand Metabolic Networks, Comparative and Functional Genomics 2:155-168, 2001.

Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).

Friscourt, F. et al., A Fluorogenic Probe for the Catalyst-Free Detection of Azide-Tagged Molecules, J. Am. Chem. Soc. 2012, 134, 18809-18815.

Friscourt et al., "Polar Dibenzocyclooctynes for Selective Labeling of Extracellular Glycoconjugates of Living Cells," J. Am. Chem. Soc., Mar. 21, 2012, 134(11):5381-5389.

Fujimore, Kenji et al., A Modeling Analysis of Monoclonal Antibody Percolation Through Tumors: A Binding-Site Barrier, J Nuc Med. 31: 1191-1198 (1990).

Fujio, M., et al. "Structure-Based Discovery of Glycolipids for CD1d-Mediated NKT Cell Activation: Tuning the Adjuvant versus Immunosuppression Activity." CAPLUS 145:240945 (2006).

Fujio, M., et al. "Structure-Based Discovery of Glycolipids for CD1d-Mediated NKT Cell Activation: Tuning the Adjuvant versus Immunosuppression Activity." J. Am. Chem. Soc. (2006), vol. 128, pp. 9022-9023.

Fukui, S et al., Oligosaccharide microarrays for high-throughput detection and specificity assignments of carbohydrate-protein interactions. Nat. Biotechnol. 20, 1011-1017, (2002).

Gabius, HJ. Tumor Lectinology: at the intersection of carbohydrate chemistry, biochemistry, cell biology and oncology. Angew. Chem. Int. Ed. Engl. 27, 1267-1276.

Gamblin, SJ et al., The Structure and Receptor Binding Properties of the 1918 Influenza Hemagglutinin, Science, 303:1838, 2004.

Garces, F. et al. Structural evolution of glycan recognition by a family of potent HIV antibodies. Cell 159, 69-79, (2014).

Gaschen, B. et al. AIDS—Diversity Considerations in HIV-I vaccine selection. Science 296, 2354-2360, (2002).

Geiler et al., Comparison of pro-inflammatory cytokine expression and cellular signal transduction in human macrophages infected with different influenza A viruses. Med Microbiol Immunol. Feb. 2011;200(1):53-60.

GenBank accession No. WP_0080769537.1, published May 10, 2013.

GenBank accession No. WP_008767711.1, published May 10, 2013.

Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).

Gerson et al., "ESR. Spectra and Structures of Radical Anions in the Dibenzo[a, e]cyclooxtene Series," Helvetica Chinica Acta, Jan. 1, 1976, 59(6): 2038-2048.

Giaccone, Giuseppe et al., "A phase I study of the natural killer T-cell ligand α-galactosylceramide (KRN7000) in patients with solid tumors," Clin. Cancer Res., Dec. 2002, 8(12):3702-3709.

Go, E. P. et al. Characterization of glycosylation profiles of HIV-I transmitted/founder envelopes by mass spectrometry. J. Virol. 85, 8270-8284, (2011).

Go, E. P. et al. Comparative Analysis of the Glycosylation Profiles of Membrane-Anchored HIV-I Envelope Glycoprotein Trimers and Soluble gp140. J. Virol. 89, 8245-57, (2015).

Godefroy, S. et al., Effect of Skin Barrier Disruption on Immune Responses to Topically Applied Cross-Reacting Material, CRM197 of Diphtheria Toxin, Infect. Immun. 2005, 73, 4803.

Goldenthal et al., "Safety Evaluation of Vaccine Adjuvants: National Cooperative Vaccine Development Working Group," AIDS Res. Hum. Retroviruses, 1993, 9(Supp.1):S47-S51.

Golkowski et al., "Strategy for catch and release of azide-tagged biomolecules utilizing a photolabile strained alkyne construct," Organic and Biomolecular Chemistry, Jan. 1, 2012, 10(23):4496.

Gordon et al., "Reactivity of biarylazacyclooctynones in copper-free click chemistry," J. Am. Chem. Soc., Jun. 6, 2012, 134(22): 9199-9208.

Govorkova et al, Combination chemotherapy for influenza. Viruses. Aug. 2010;2(8):1510-29.

Graham, Duncan et al., Surface-Enhanced Resonance Raman Scattering as a Novel Method of DNA Discrimination, Angew. Chem., 2000, 112(6), 1103-1105.

Grandjean, C. et al., On the Preparation of Carbohydrate-Protein Conjugates Using the Traceless Staudinger Ligation, J Org Chem 2005, 70, 7123-7132.

Greenbaum et al., "Chemical approaches for functionally probing the proteome," Mol. Cell. Proteomics, 2002, 1:60-68.

Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.

Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.

Gulland, Fire Cases of Spread of Oseltamivir Resistant Swine Flu Between Patients are Reported in Wales, BMJ, Nov. 23, 2009;339:b4975.

Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.

(56) References Cited

OTHER PUBLICATIONS

Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," *J. Immuol.*, May 1, 1995, 154(9):4322-4332.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hasegawa, Akira, et al., Synthesis of Sialyl Lewis X Ganglioside Analogues Containing Modified L-Fucose Residues, Carbohydr. Res. 1995, 274, 165-181.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Hirabayashi, J. et al., Oligosaccharide Microarrays for Glycomics, Trends in Biotechnology 21 (4): 141-143, 2003.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," *Immunol. Today*, Jun. 1992, 13(6):198-200.
Hsu et al., "Alkynyl sugar analogs for the labeling and visualization of glycoconjugates in cells," *Proc. Natl. Acad. Sci. USA*, Feb. 20, 2007, 104(8), 2614-2619.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Immunogenicity, Wikipedia p. 1-3. Downloaded on Aug. 16, 2016 from https://en.wikipedia.org/wild/Immunogenicity. (2016).
International Search Report and Written Opinion issued for International application No. PCT/US2015/011748, dated Aug. 21, 2015, 17 pages.
International Search Report dated Jan. 13, 2012, from corresponding International Patent Application No. PCT/US2011/035982, 17 pages.

International Search Report dated Nov. 13, 2014, from corresponding International Patent Application No. PCT/US2014/054617, 10 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihero et al., A Novel Ganglioside Isolated From Renal Cell Carcinoma, Biol Chem 2001, 276, 16695.
Jacobs et al., "Metabolic labeling of glycoproteins with chemical tags through unnatural sialic acid biosynthesis," *Methods Enzymol.*, 2000, 327:260-275.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, a. et al., "BODIPY dyes in photodynamic therapy." Chem. Soc. Rev. 2013, 42, 77-88.

(56) References Cited

OTHER PUBLICATIONS

Kawakami et al., "Critical role of Vα14+ natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of v$_\alpha$14 NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karmakar, M. et al., Current Trends in Research and Application of Microbial Cellulases, Research Journal of Microbiology, (2001) 6(1): 41-53.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active Methionine Analogues in *Escherichia coli*, tetrahedron 56:9487, 2001.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "α-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kos, "Regulation of adaptive immunity by natural killer cells," *Immunol. Res.*, 1998, 17(3):303-312.
Koshihara et al., 1984, Biochmica et biophysica acta, 792(1), pp. 92-97.
Kotteas et al., Immunotherapy for pancreatic cancer, J cancer Res Clin Oncol, 142(8): 1795-1805, 2016.

Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific CD4+ and CD4−8−T cells in mice and humans," *J. Exp. Med.*, Sep. 1, 1994, 180(3):1097-1106.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lemieux, R. U. et al., Halide ion catalyzed glycosidation reactions. Syntheses of a-linked disaccharides. J Am. Chem. Soc. 97(14), 4056-62, (1975).
Lew et al., Discovery and Development of GS 4104 (oseltamivir): an Orally Active Influenza Neuraminidase Inhibitor, Curr Med Chem, Jun. 2000, 7(6):663-672.
Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification ofxanthone and xanthene-based fluorophores using click chemistry." Org. Lett. 2009, 11, 3008-3011.
Li, Lingling, et al., "Syntheses and spectral properties of functionalized, water-soluble BODIPY derivatives." *J. Org. Chem.* 2008, 73, 1963-1970.
Li, L. et al. Efficient chemoenzymatic synthesis of an N-glycan isomer library. Chem. Sci. 6, 5652-5661 (2015).
Liang et al., "Quantitative microarray analysis of intact glycolipid-CD1d interaction and correlation with cell-based cytokine production," *J. Am. Chem. Soc.*, Sep. 17, 2008, 130(37):12348-12354.

(56) References Cited

OTHER PUBLICATIONS

Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H., Quantitative analysis of Carbohydrate-Protein Interactions Using Glycan Microarrays: Determination of Surface and Solution Dissociation Constants. J. Amer. Chem. Sci. 2007, 129, 11177-11184.
Liu et al., "Activity-based protein profiling: the serine hydrolases," Proc. Natl. Acad. Sci. USA, Dec. 21, 1999, 96(26):14694-14699.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Nad Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Lu et al., "Design of a mechanism-based probe for neuraminidase to capture influenza viruses," Angew. Chem. Int. Ed. Engl., Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
MacBeath, G. and Schreiber, S. L., Printing Proteins as Microarrays for High-Throughput Function Determination, Science, 289, 1760-1763, 2000.
Makino et al., Predominant expression of invariant $V_\alpha 14^+$ TCR α chain in $NK1.1^+$ T cell populations, Int. Immunol., Jul. 1995, 7(7):1157-1161.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).
Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R., IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," Nat. Biotechnol., Oct. 1999, 17(10):969-973.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Milstein, C & Cuello, AC, Hybrid Hydridomas and their use in immunohistochemistry, Nature 305, 537-540, Oct. 1993.

Miyagi et al., "Mammalian sialidases: Physiological and pathological roles in cellular functions," Glycobiology, Jul. 2012, 22(7):880-896.
Miyagi et al., "Plasma membrane-associated sialidase as a crucial regulator of transmembrane signalling," J. Biochem., Sep. 2008, 144(3):279-285.
Miyagi et al., "Sialidase and malignancy: a minireview," Glycoconj. J., 2004, 20(3):189-198.
Miyagi, "Aberrant expression of sialidase and cancer progression," Proc. Jpn. Acad. Ser. B. Phys. Biol. Sci., 2008(10), 84:407-418.
Miyaji, E. N. et al., Induction of Neutralizing Antibodies Against Diphtheria Toxin by Priming with Recombinant Mycobacterium bovis BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H 2$ bias of natural killer T cells," Nature, Oct. 4, 2001, 413(6855):531-534.
Monti et al., "Sialidases in vertebrates: a family of enzymes tailored for several cell functions," Adv. Carbohydr. Chem. Biochem., 2010, 64:403-479.
Moody, M. D. et al., Array-based ELISAs for High-Throughput Analysis of Human Cytokines. Biotechniques (2001), 31, 186-194.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," Immunol. Today, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Ni, Jing et al., Immunoassay Readout Method Using Extrinsic Raman Labels Adsorbed on Immunogold Colloids, Anal. Chem., 1999, 71(21), pp. 4903-4908.
Nieuwenhuis et al., "CD1d-dependent macrophage-mediated clearance of Pseudomonas aeruginosa from lung," Nat. Med., Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," Proc. Natl. Acad. Sci. USA, Jul. 1985, 82(14):4592-4596.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.

(56) References Cited

OTHER PUBLICATIONS

O'Garra, "Cytokines induce the development of functionally heterogeneous T helper cell subsets," Immunity, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," Adv. Immunol., 1998, 70:281-312.
Otsubo N, et al., An Efficient and Straightforward Synthesis of Sialyl Lex Glycolipid as a Potent Selectin Blocker [[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," Biochemistry, Jan. 16, 2007, 46(2):350-358.
Paulson, J. C., Blixt, 0. & Collins, B. E. Sweet spots in functional glycomics. Nat. Chem. Biol. 2, 238-248, (2006).
Peelle et al., "Characterization and use of green fluorescent proteins from Renilla mulleri and Ptilosarcus guernyi for the human cell display of functional peptides," J. Protein Chem., Aug. 2001, 20(6):507-519.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," Immunity, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-585 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Poloukhtine et al., "Selective labeling of living cells by a photo-triggered click reaction," J. Am. Chem. Soc., Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium ( 4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4"-deoxy and -fluoro analogs of the immunostimulatory glycolipid, KRN7000," Bioorg. Med. Chem. Lett., 2009, 19:4122-4125.
Rana, G. Kucukayan-Dogu, E. Bengu "Growth of vertically aligned carbon nanotubes over self-ordered nano-porous alumina films and their surface properties"0 Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human lgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Romagnani, "Induction of $T_H1$ and $T_H2$ responses: a key role for the 'natural' immune response?" Immunol. Today, Oct. 1992, 13(10):379-381.
Rosenstein, N.E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," Angew. Chem. Int. Ed. Engl., Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rudnick et al., Affinity and Avidity in Antibody-Based Tumor Targeting, Can Biotherp & Radoipharm, 24, 155-162 (2009).
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.

(56) References Cited

OTHER PUBLICATIONS

Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." *Proc. Nat. Acad. Sci. U.S.A.*, 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shie, Jiun-Jie et al., "A concise and flexible synthesis of the potent anti-influenza agents tamiflu and tamiphosphor," Angew. Chem. Int. Ed Engl., 2008, 47(31):5788-5791.

Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sieber et at, "Proteomic profiling of metalloprotease activities with cocktails of active-site probes," *Nat. Chem. Biol.*, May 2006, 2(5):274-281.
Sivakumar, Krishnamoorthy et al., "A fluorogenic 1,3-dipolar cycloaddition reaction of 3-azidocoumarins and acetylenes." *Org. Lett.* 2004,24, 4603-4606.
Skehel, John et al., Receptor Binding and Membrane Fusion in Virus Entry: The Influenza Hemagglutinin, Ann. Rev Biochem, 69:531, 2000.
Sletten et al., "Bioorthogonal Chemistry: Fishing for Selectivity in a Sea of Functionality," *Angew. Che. Int. Ed. Engl.*, Aug. 27, 2009, 48(38):6974-6998.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced By 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun. 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.

(56) References Cited

OTHER PUBLICATIONS

Stubbs et al., "Synthesis and use of mechanism-based protein-profiling probes for retaining β-D-glucosaminidases facilitate identification of Pseudomonas aeruginosa NagZ," *J. Am. Chem. Soc.*, Jan. 9, 2008, 130(1):327-335.
Su, G. Hahner, W. Thou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Supplementary European Search Report in European Application No. EP 13775664.9, dated Oct. 27, 2015, in 7 pages.
Sutton, VR et al., Bcl-2 Prevents Apoptosis Induced by Perforin and Granzyme B, But Not That Mediated by Whole Cytotoxic Lymphocytes, J of Immunology 1997, 158(12), 5783.
Tahir et al., "Loss of IFN-γ production by invariant NK T cells in advanced cancer,"0 *J. Immunol.*, Oct. 1, 2001, 167(7):4046-4050.
Takakura, Yoshimitsu et al., Molecular cloning, expression and properties of an alpha/beta-Galactoside alpha 2,3-sialyltransferase from *Vibrio* sp. JT-FAJ-16. J. Biochem. 142, 403-412, (2007).
Takano, Rya et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Toba et al. "Synthesis and biological evaluation of truncated α-glaactosylceramide derivatives focusing on cytokine induction profile," Bioorganic & Medicinal Chemistry 20(2012): 2850-2859.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Charng-sheng et al., Development of Trifunctional Probes for Glycoproteomic Analysis, Chem. Commun. 2010, 46, 5575-5577.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," *Nature*, Apr. 26, 2007, 446(7139):1023-1029.
Vasella et al., "Synthesis of a phosphonic acid analogue of N-Acetyl-2,3-didehydro-2-deoxyneuraniinic acid, an inhibitor of Vibrio cholerae sialidase," Helv. Chim. Acta, Mar. 13, 1991, 74(2):451-463.
Vavricka, Christopher et al., Influenza Neuraminidase Operates Via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.

(56) References Cited

OTHER PUBLICATIONS

Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherapy Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yuen et al., Human infection by avian influenza A H5N1. Hong Kong Med J. Jun. 2005;1 1(3):189-99.
Zhang et al., "New cerebrosides from Acanthopanax gracilistylus," CAPLUS 156:225776 (2011).
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gpl20 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.

(56) References Cited

OTHER PUBLICATIONS

Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, Aug. 7, 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
Chu, Kuo-Ching et al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.
Frank, Natasha et al., The Therapeutic Promise of the Cancer Stem Cell Concept, Journal of Clinical Investigation, 120(1) 41-50, Jan. 2010.
Hsu, Nien-Yeen et al., Desorption Ionization of Biomolecules on Metals, Anal. Chem., 80, 5203-5210, 2008.
Katagiri, Yohko et al Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.
Merck, MAB4304, Anti-Stage-Specific Embryonic Antigen-4 Antibody, Clone MC-813-70, 4 Pages, 2017.
Moal, E. Le et al., Enhanced Fluorescence Cell Imaging with Metal-Coated Slides, Biophysical Journal, vol. 92, 2150-2161, Mar. 2007.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Pan, Yanbin et al., Synthesis and Immunological Properties of N-Modified GM3 Antigens as Therapeutic Cancer Vaccines, J. Med. Chem., 48(3), 875-883, 2005.
Shevinsky, LH et al., Monoclonal Antibody to Murine Embryos Defines a Stage-Specific Embryonic Antigen Expressed on Mouse Embryos and Human Teratocarinoma Cells., CELL vol. 30, Issue 3, Oct. 1982, pp. 697-705.
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Cheung et al., Meeting Info: 23rd International Symposium on Glycoconjugates, Glyco 23. Split, Croatia. Sep. 15, 2015-Sep. 20, 2015, vol. 32, No. 5, pp. 323.
International Search Report and Written Opinion in International Application No. PCT/US2017/048074, dated Dec. 26, 2017, 17 pages.
Lei, Jianqing et al., Potential antitumor applications of a monoclonal antibody specifically targeting human papilloma virus 16 E749-57 peptide, Microbiology and Immunology, 2012, vol. 56, pp. 456-462.
Tsai, Charng-Sheng et al., Cell-Permeable Probe for Identification and Imaging of Sialidases, PNAS, vol. 110, No. 7, 2013, 2466-2471.

\* cited by examiner

ANTI-HER2 GLYCOANTIBODIES AND USES THEREOF

RELATED APPLICATIONS

This application claims the benefit of priority to U.S. provisional applications U.S. Ser. No. 62/003,104, filed May 27, 2014, U.S. Ser. No. 62/020,199, filed Jul. 2, 2014, and U.S. Ser. No. 62/110,338, filed Jan. 30, 2015. The contents of each of which is hereby incorporated by reference in its entirety.

BACKGROUND OF THE INVENTION

Fc glycosylation has been an important subject in the field of therapeutic monoclonal antibodies. Fc glycosylation can significantly modify Fc effector functions such as Fc receptor binding and complement activation, and thus affect the in vivo safety and efficacy profiles of therapeutic antibodies.

Several expression systems based on genetically engineering have been reported to produce therapeutic monoclonal antibodies. These include yeasts such as *Pichia pastoris*, insect cell lines, and even bacteria. However, these expression systems suffer from a number of drawbacks that can negatively affect the effector function of therapeutic antibodies.

The majority of approved biopharmaceuticals are produced in mammalian cell culture systems to deliver proteins with desired glycosylation patterns and thus ensure reduced immunogenicity and higher in vivo efficacy and stability. Non-human mammalian expression systems such as CHO or NS0 cells have the machinery required to add complex, human-type glycans. However, glycans produced in these systems can differ from glycans produced in humans. Their glycosylation machinery often adds undesired carbohydrate determinants which may alter protein folding, induce immunogenicity, and reduce circulatory life span of the drug. Notably, sialic acid as N-acetylneuraminic acid is not efficiently added in most mammalian cells and the 6-linkage is missing in these cells. Engineering cells with the various enzymatic activities required for sialic acid transfer has not yet succeeded in providing a human-like pattern of glycoforms to protein drugs. To date, there is a need for engineering animal cells or glycoproteins to highly sialylated products that resemble as closely as possible to human proteins.

Furthermore, mammalian cell culture delivers a heterogeneous mixture of glycosylation patterns which do not all have the same properties. Properties like safety, efficacy and the serum half-life of therapeutic proteins can be affected by these glycosylation patterns.

Trastuzumab (Herceptin®), approved in 1998 for the treatment of patients with HER2-overexpressing metastatic breast cancers (Baselga et al, (1996) J. Clin. Oncol. 14:737-744), is a humanized anti-HER2 IgG antibody that binds to the extracellular component of the Her2/neu receptor. Overexpression of HER2 is observed in approximately 20% of human breast cancers (hereinafter referred to as HER2-positive breast cancer) and is implicated in the aggressive growth and poor clinical outcomes associated with these tumors (Slamon et al (1987) Science 235: 177-182). Trastuzumab functions with a variety of different of mechanisms, but the main action is to bind to the extracellular membrane portion of the Human Epidermal growth factor Receptor 2 (HER-2) on the surface of cancer cells, preventing the activation of its intra cellular tyrosine kinase. Herceptin acts on the immune system mediating Antibody Dependent Cellular Cytotoxicity (ADCC) and can fix complement, but is considered unable to mediate Complement Dependent Cell Cytotoxicity (CDC).

Trastuzumab is produced in Chinese hamster ovary (CHO) cells and is highly heterogeneous in glycosylation patterns in the Fc domain. Each of anti-HER2 IgG molecules in the heterogeneous mixture may not all have the same property, and certain N-linked oligosaccharides bound to therapeutic proteins may trigger undesired effects in patients thus deeming them a safety concern. Response rates to the antibody Trastuzumab given as a single agent (monotherapy) have ranged from about 15-26%.

SUMMARY OF THE INVENTION

Accordingly, one aspect of the present disclosure relates to a composition of anti-HER2 glycoantibodies comprising a homogeneous population of anti-HER2 IgG molecules having the same N-glycan on each of Fc. The anti-HER2 glycoantibodies of the invention can be produced from anti-HER2 monoclonal antibodies by Fc glycoengineering. Importantly, the anti-HER2 glycoantibodies have improved therapeutic values with increased ADCC activity or increased Fc receptor binding affinity compared to the corresponding monoclonal antibodies that have not been glycoengineered.

As used herein, the term "anti-HER2 glycoantibodies" ("anti-HER2 GAbs") refers to a homogeneous population of anti-HER2 IgG molecules having the same glycoform on Fc. The term "anti-HER2 glycoantibody" ("anti-HER2 GAb") refers to an individual IgG molecule in the anti-HER2 glycoantibodies.

In preferred embodiments, the N-glycan is attached to the Asn-297 of the Fc region.

In some embodiments, the anti-HER2 glycoantibody described herein comprises a heavy chain having the amino acid sequence set forth in SEQ ID NO: 1, and a light chain having the amino acid sequence set forth in SEQ ID NO: 2. In a preferred embodiment, the glycoantibody comprises a light chain sequence and a heavy chain sequence of Trastuzumab (Herceptin®).

Disclosed herein are a number of functionally active anti-HER2 glycoantibodies constructed by Fc glycoengineering from Trastuzumab. Importantly, anti-HER2 glycoantibodies with optimized glycoforms exhibit improved ADCC activities as compared to Trastuzumab. This is the first report that shows homogeneously Fc-glycosylated anti-HER2 antibodies with improved ADCC activity have been successfully generated.

In some embodiments, the anti-HER2 glycoantibodies described herein are characterized in that the glycoantibodies exhibit enhanced binding to FcγRIIIA as compared to Trastuzumab.

In some embodiments, the N-glycan described herein has a biantennary structure. In some embodiments, the N-glycan comprises a bisecting GlcNAc.

In some embodiments, the N-glycan described herein comprises at least one α2-6 terminal sialic acid. In certain embodiments, the N-glycan comprises one α2-6 terminal sialic acid. In a preferred embodiment, the N-glycan comprises two α2-6 terminal sialic acids.

In some embodiments, the N-glycan described herein comprises at least one α2-3 terminal sialic acid. In certain embodiments, the N-glycan comprises one α2-3 terminal sialic acid. In a preferred embodiment, the N-glycan comprises two α2-3 terminal sialic acids.

In some embodiments, the N-glycan described herein comprises at least one galactose. In certain embodiments, the N-glycan comprises one galactose. In a preferred embodiment, the N-glycan comprises two galactoses.

Preferably, the N-glycan according to the disclosure is free of core fucose.

In some embodiments, the N-glycan described herein has the sequence selected from the group consisting of $Sia_2(\alpha2\text{-}6)Gal_2GlcNAc_2Man_3GlcNAc_2$, $Sia_2(\alpha2\text{-}6)Gal_2GlcNAc_3Man_3GlcNAc_2$, $Sia_2(\alpha2\text{-}3)Gal_2GlcNAc_2Man_3GlcNAc_2$, $Sia_2(\alpha2\text{-}3)Gal_2GlcNAc_3Man_3GlcNAc_2$, $Sia_2(\alpha2\text{-}3/\alpha2\text{-}6)Gal_2GlcNAc_2Man_3GlcNAc_2$, $Sia_2(\alpha2\text{-}6/\alpha2\text{-}3)Gal_2GlcNAc_2Man_3GlcNAc_2$, $Sia_2(\alpha2\text{-}3/\alpha2\text{-}6)Gal_2GlcNAc_3Man_3GlcNAc_2$, $Sia_2(\alpha2\text{-}6/\alpha2\text{-}3)Gal_2GlcNAc_3Man_3GlcNAc_2$, $Sia(\alpha2\text{-}6)Gal_2GlcNAc_3Man_3GlcNAc_2$, $Sia(\alpha2\text{-}6)Gal_2GlcNAc_2Man_3GlcNAc_2$, $Sia(\alpha2\text{-}3)Gal_2GlcNAc_2Man_3GlcNAc_2$, $Sia(\alpha2\text{-}6)Gal_2GlcNAc_2Man_3GlcNAc_2$, $Sia(\alpha2\text{-}3)Gal_2GlcNAc_3Man_3GlcNAc_2$, $Sia(\alpha2\text{-}6)Gal_2GlcNAc_3Man_3GlcNAc_2$, $Sia(\alpha2\text{-}3)GalGlcNAc_2Man_3GlcNAc_2$, $Sia(\alpha2\text{-}6)GalGlcNAc_2Man_3GlcNAc_2$, $Sia(\alpha2\text{-}3)GalGlcNAc_3Man_3GlcNAc_2$, $GalGlcNAc_3Man_3GlcNAc_2$, $Gal_2GlcNAc_2Man_3GlcNAc_2$, $Gal_2GlcNAc_3Man_3GlcNAc_2$, $GalGlcNAc_2Man_3GlcNAc_2$, $GalGlcNAc_3Man_3GlcNAc_2$, $GlcNAc_3Man_3GlcNAc_2$, $GlcNAc_2Man_3GlcNAc_2$, $GlcNAcMan_3GlcNAc_2$ and $Man_3GlcNAc_2$.

In preferred embodiments, the N-glycan described herein has the sequence selected from the group consisting of $Sia_2(\alpha2\text{-}6)Gal_2GlcNAc_2Man_3GlcNAc_2$, $Sia_2(\alpha2\text{-}6)Gal_2GlcNAc_3Man_3GlcNAc_2$, $Sia_2(\alpha2\text{-}3)Gal_2GlcNAc_2Man_3GlcNAc_2$, $Sia_2(\alpha2\text{-}3)Gal_2GlcNAc_3Man_3GlcNAc_2$, $Sia_2(\alpha2\text{-}3/\alpha2\text{-}6)Gal_2GlcNAc_2Man_3GlcNAc_2$, $Sia_2(\alpha2\text{-}6/\alpha2\text{-}3)Gal_2GlcNAc_2Man_3GlcNAc_2$, $Sia_2(\alpha2\text{-}3/\alpha2\text{-}6)Gal_2GlcNAc_3Man_3GlcNAc_2$, $Sia_2(\alpha2\text{-}6/\alpha2\text{-}3)Gal_2GlcNAc_3Man_3GlcNAc_2$, $Sia(\alpha2\text{-}6)Gal_2GlcNAc_3Man_3GlcNAc_2$, $Sia(\alpha2\text{-}3)Gal_2GlcNAc_2Man_3GlcNAc_2$, $Sia(\alpha2\text{-}6)Gal_2GlcNAc_2Man_3GlcNAc_2$, $Sia(\alpha2\text{-}3)Gal_2GlcNAc_3Man_3GlcNAc_2$, $Sia(\alpha2\text{-}6)Gal_2GlcNAc_3Man_3GlcNAc_2$, $Sia(\alpha2\text{-}3)GalGlcNAc_2Man_3GlcNAc_2$, $Sia(\alpha2\text{-}6)GalGlcNAc_2Man_3GlcNAc_2$, $Sia(\alpha2\text{-}3)GalGlcNAc_3Man_3GlcNAc_2$, $Gal_2GlcNAc_2Man_3GlcNAc_2$ and $Gal_2GlcNAc_3Man_3GlcNAc_2$.

Another aspect of the present disclosure features a pharmaceutical formulation comprising a composition of anti-HER2 glycoantibodies or antigen binding fragments thereof described herein and a pharmaceutically acceptable carrier.

The pharmaceutical formulation according to the disclosure may be used in therapeutics. Anti-HER2 GAb molecules of the present invention are useful for treating and diagnosing human diseases related to HER2. In preferred embodiments, anti-HER2 GAb molecules are administered to a patient with breast cancer or other HER2-related tumors or other diseases.

Disclosed herein include methods for treating HER2-expressing cancer in a patient, the method comprising administering to the patient an effective amount of a pharmaceutical composition described herein.

In some embodiments, the HER2-expressing cancer is breast cancer.

Anti-HER2 GAb molecules of the present invention may be administered in combination with other anticancer therapies including but not limited to chemo- and radio-therapies, and in combination with some cytokines, such as G-CSF in certain other cases.

In addition, the disclosure also provides combination pharmaceutical compositions suitable for monotherapy or combination therapy that comprises substantially homogeneous glycoantibodies described herein and other antibodies and/or other therapeutic agents. The pharmaceutical composition can be administered as coformulation or used in co-administration therapeutic regimen.

The anti-HER2 glycoantibodies described herein may be generated from anti-HER2 monoclonal antibodies approved by FDA or in development. The anti-HER2 monoclonal antibodies may be humanized, human or chimeric.

The anti-HER2 glycoantibodies described herein may be produced in vitro. The anti-HER2 glycoantibodies may be generated by Fc glycoengineering. In certain embodiments, the anti-HER2 glycoantibodies are enzymatically or chemoenzymatically engineered from the anti-HER2 monoclonal antibodies obtained by mammalian cell culturing.

In yet another aspect, the present disclosure relates to a method of making an anti-HER2 glycoantibody, the method comprising: (a) contacting an anti-HER2 monoclonal antibody with an alpha-fucosidase and at least one endoglycosidase, thereby an anti-HER2 monoclonal antibody bearing a defucosylated monosaccharide GlcNAc on the Fc is produced, and (b) adding an carbohydrate moiety to GlcNAc under suitable conditions.

In some embodiments, the anti-HER2 monoclonal antibody used for making an anti-HER2 glycoantibody is Trastuzumab (Herceptin®).

In some embodiments, the carbohydrate moiety is selected from the group consisting of $Sia_2(\alpha2\text{-}6)Gal_2GlcNAc_2Man_3GlcNAc$, $Sia_2(\alpha2\text{-}6)Gal_2GlcNAc_3Man_3GlcNAc$, $Sia_2(\alpha2\text{-}3)Gal_2GlcNAc_2Man_3GlcNAc$, $Sia_2(\alpha2\text{-}3)Gal_2GlcNAc_3Man_3GlcNAc$, $Sia_2(\alpha2\text{-}3/\alpha2\text{-}6)Gal_2GlcNAc_2Man_3GlcNAc$, $Sia_2(\alpha2\text{-}6/\alpha2\text{-}3)Gal_2GlcNAc_2Man_3GlcNAc$, $Sia_2(\alpha2\text{-}3/\alpha2\text{-}6)Gal_2GlcNAc_3Man_3GlcNAc$, $Sia_2(\alpha2\text{-}6/\alpha2\text{-}3)Gal_2GlcNAc_3Man_3GlcNAc$, $Sia(\alpha2\text{-}6)Gal_2GlcNAc_3Man_3GlcNAc$, $Sia(\alpha2\text{-}3)Gal_2GlcNAc_3Man_3GlcNAc$, $Sia(\alpha2\text{-}6)Gal_2GlcNAc_2Man_3GlcNAc$, $Sia(\alpha2\text{-}3)Gal_2GlcNAc_2Man_3GlcNAc$, $Sia(\alpha2\text{-}6)Gal_2GlcNAc_3Man_3GlcNAc$, $Sia(\alpha2\text{-}3)GalGlcNAc_2Man_3GlcNAc$, $Sia(\alpha2\text{-}6)GalGlcNAc_2Man_3GlcNAc$, $Sia(\alpha2\text{-}3)GalGlcNAc_3Man_3GlcNAc$, $GalGlcNAc_3Man_3GlcNAc$, $Gal_2GlcNAc_2Man_3GlcNAc_2$, $Gal_2GlcNAc_3Man_3GlcNAc$, $GalGlcNAc_2Man_3GlcNAc$, $GalGlcNAc_3Man_3GlcNAc$, $GlcNAc_3Man_3GlcNAc$, $GlcNAc_2Man_3GlcNAc$, $GlcNAcMan_3GlcNAc$ and $Man_3GlcNAc$.

In preferred embodiments, the carbohydrate moiety is selected from the group consisting of $Sia_2(\alpha2\text{-}6)Gal_2GlcNAc_2Man_3GlcNAc$, $Sia_2(\alpha2\text{-}6)Gal_2GlcNAc_3Man_3GlcNAc$, $Sia_2(\alpha2\text{-}3)Gal_2GlcNAc_2Man_3GlcNAc$, $Sia_2(\alpha2\text{-}3)Gal_2GlcNAc_3Man_3GlcNAc$, $Sia_2(\alpha2\text{-}3/\alpha2\text{-}6)Gal_2GlcNAc_2Man_3GlcNAc$, $Sia_2(\alpha2\text{-}6/\alpha2\text{-}3)Gal_2GlcNAc_2Man_3GlcNAc$, $Sia_2(\alpha2\text{-}3/\alpha2\text{-}6)Gal_2GlcNAc_3Man_3GlcNAc$, $Sia_2(\alpha2\text{-}6/\alpha2\text{-}3)Gal_2GlcNAc_3Man_3GlcNAc$, $Sia(\alpha2\text{-}6)Gal_2GlcNAc_3Man_3GlcNAc$, $Sia(\alpha2\text{-}3)Gal_2GlcNAc_2Man_3GlcNAc$, $Sia(\alpha2\text{-}6)Gal_2GlcNAc_2Man_3GlcNAc$, $Sia(\alpha2\text{-}3)Gal_2GlcNAc_3Man_3GlcNAc$, $Sia(\alpha2\text{-}6)Gal_2GlcNAc_3Man_3GlcNAc$, GalGlcNAc$_2$Man$_3$GlcNAc, Sia($\alpha$2-3)
GalGlcNAc$_2$Man$_3$GlcNAc, Sia($\alpha$2-6)
GalGlcNAc$_3$Man$_3$GlcNAc, Sia($\alpha$2-3)
GalGlcNAc$_3$Man$_3$GlcNAc, Gal$_2$GlcNAc$_2$Man$_3$GlcNAc and Gal$_2$GlcNAc$_3$Man$_3$GlcNAc.

The adding in step (b) can be performed by a transglycosylase. Transglycosylase includes, but are not limited to, EndoS, EndoH, EndoA and EndoM.

Endoglycosidases useful for the method of the invention include, but are not limited to, EndoS, EndoH, EndoA, EndoM and Endo-F3.

In some embodiments, the alpha-fucosidase comprises a polypeptide having an amino acid sequence at least about 90%, 91%, 92%, 93%, 94%, 95%, 96%, 97%, 98%, 99% identical to SEQ ID NO: 5.

In certain embodiments, the alpha-fucosidase is a recombinant *Bacteroides* alpha-L-fucosidase.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

FIG. 5 discloses "EEQYNSTYR" as SEQ ID NO: 4.

FIG. 6 discloses "EEQYNSTYR" as SEQ ID NO: 4.

DETAILED DESCRIPTION OF THE INVENTION

Figure 1:
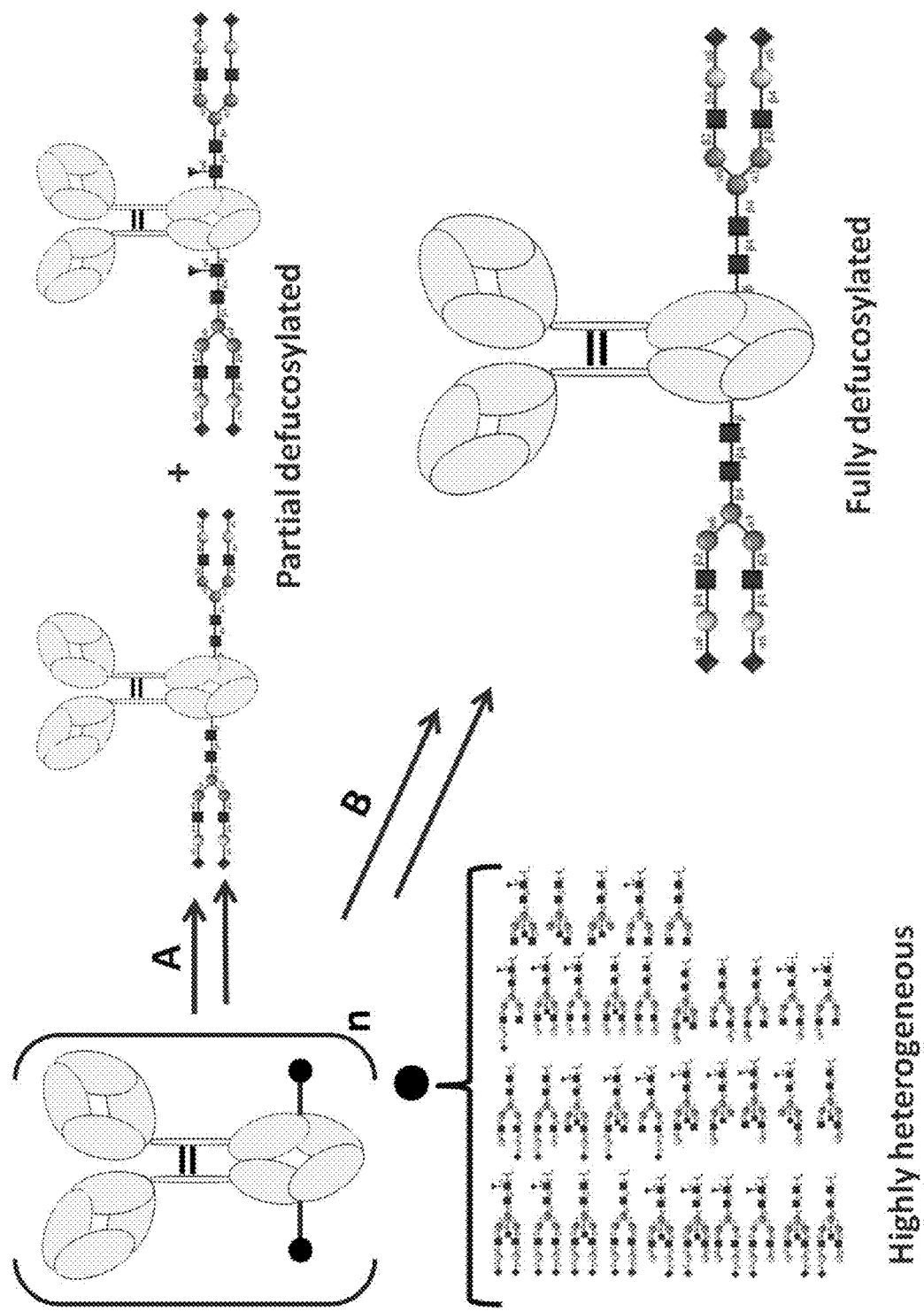
FIG. 1 shows a schematic representation of Fc glycoengineering of monoclonal antibodies. Route (A) shows the methods known in the art that lead to a mixture of fucosylated and nonfucosylated antibodies. Route (B) shows the method of the present invention that leads to a homogeneous glycoantibodies.
Figure 2:
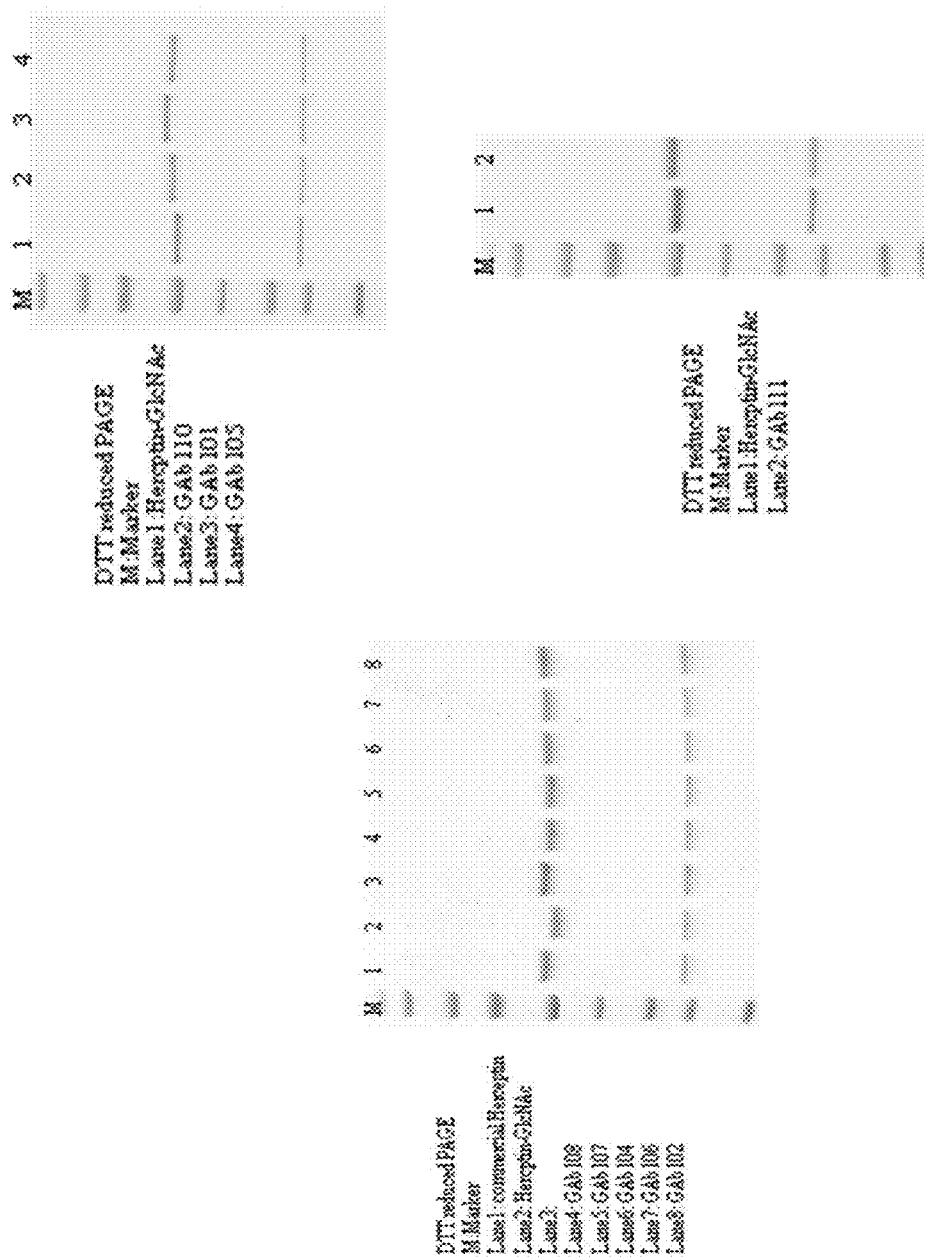
FIG. 2 shows SDS-PAGE analyses of anti-HER2 GAbs 102, 102, 104, 105, 106, 107, 108, 110 and 111.

Accordingly, a need remains for improving monoclonal antibody therapy with improved anti-HER2 antibodies. A few specific glycoforms in the heterogeneous mixtures of glycosylation patterns are known to confer desired biological functions. Thus, it is of great interest to generate therapeutic antibodies contain a well-defined glycan structure and sequence as desired glycoforms for therapeutic purposes.

The present disclosure relates to the development of a novel class of monoclonal antibodies, named "glycoantibodies". The term "glycoantibodies" was coined by the inventor, Dr. Chi-Huey Wong, to refer to a homogeneous population of monoclonal antibodies (preferably, therapeutic monoclonal antibodies) having a single, uniform glycoform on Fc. The individual glycoantibodies comprising the homogeneous population are identical, bind to the same epitope, and contain the same Fc glycan with a well-defined glycan structure and sequence.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

Definitions:

As used herein, the term "glycan" refers to a polysaccharide, oligosaccharide or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of $\beta$-1,4-linked D-glucose, and chitin is a glycan composed of $\beta$-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the terms "fucose", "core fucose" and "core fucose residue" are used interchangeably and refer to a fucose in $\alpha$1,6-position linked to the N-acetylglucosamine.

As used herein, the term "fucosylated" refers to the presence of a core fucose in the N-glycan of Fc, whereas the term "defucosylated" refers to the absence of a core fucose in the N-glycan of Fc.

As used herein, the terms "N-glycan", "N-linked glycan", "N-linked glycosylation", "Fc glycan" and "Fc glycosylation" are used interchangeably and refer to an N-linked oligosaccharide attached by an N-acetylglucosamine (GlcNAc) linked to the amide nitrogen of an asparagine residue in a Fc-containing polypeptide. The term "Fc-containing polypeptide" refers to a polypeptide, such as an antibody, which comprises an Fc region.

As used herein, the term "glycosylation pattern" and "glycosylation profile" are used interchangeably and refer to the characteristic "fingerprint" of the N-glycan species that have been released from a glycoprotein or antibody, either enzymatically or chemically, and then analyzed for their carbohydrate structure, for example, using LC-HPLC, or MALDI-TOF MS, and the like. See, for example, the review in Current Analytical Chemistry, Vol. 1, No. 1 (2005), pp. 28-57; herein incorporated by reference in its entirety.

As used herein, the term "glycoengineered Fc" when used herein refers to N-glycan on the Fc region has been altered or engineered either enzymatically or chemically. The term "Fc glycoengineering" as used herein refers to the enzymatic or chemical process used to make the glycoengineered Fc. Exemplary methods of engineering are described in, for example, Wong et al U.S. Ser. No. 12/959,351, the contents of which is hereby incorporated by reference.

The term "effector function" as used herein refers to a biochemical event that results from the interaction of an antibody Fc region with an Fc receptor or ligand. Exemplary "effector functions" include complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions can be assessed using various assays known in the art.

As used herein, the term "Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

The term "Complement dependent cytotoxicity" or "CDC" as used herein refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR is typically no more than 6 in the H chain, and in the L chain, no more than 3. The humanized antibody optionally also will comprise at least a portion of an immunoglobulin constant region (Fc), typically that of a human immunoglobulin. For further details, see Jones et al., *Nature* 321:522-525 (1986); Reichmann et al., *Nature* 332:323-329 (1988); and Presta, *Curr. Op. Struct. Biol.* 2:593-596 (1992).

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

Administration "in combination with" one or more further therapeutic agents includes simultaneous (concurrent) and consecutive administration in any order.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™

The term "glycoantibodies" was coined by the inventor, Dr. Chi-Huey Wong, to refer to a homogeneous population of monoclonal antibodies (preferably, therapeutic monoclonal antibodies) having a single, uniformed glycoform bound to the Fc region. The individual glycoantibodies comprising the essentially homogeneous population are identical, bind to the same epitope, and contain the same Fc glycan with a well-defined glycan structure and sequence.

The terms "homogeneous", "uniform", "uniformly" and "homogeneity" in the context of a glycosylation profile of Fc region are used interchangeably and are intended to mean a single glycosylation pattern represented by one desired N-glycan species, with little or no trace amount of precursor N-glycan. In certain embodiments, the trace amount of the precursor N-glycan is less than about 2%.

"Essentially pure" protein means a composition comprising at least about 90% by weight of the protein, based on total weight of the composition, including, for example, at least about 91%, at least about 92%, at least about 93%, at least about 94%, at least about 95%, at least about 96%, at least about 97%, at least about 98%, or at least about 99% by weight.

"Essentially homogeneous" protein means a composition comprising at least about 98% by weight of protein, including for example, at least about 98.5%, at least about 99% based on total weight of the composition. In certain embodiments, the protein is an antibody, structural variants, and/or antigen binding fragment thereof.

As used herein, the terms "IgG", "IgG molecule", "monoclonal antibody", "immunoglobulin", and "immunoglobulin molecule" are used interchangeably. As used herein, "molecule" can also include antigen binding fragments.

As used herein, the term "Fc receptor" or "FcR" describes a receptor that binds to the Fe region of an antibody. The preferred FcR is a native sequence human FcR. Moreover, a preferred FcR is one which binds an IgG antibody (a gamma receptor) and includes receptors of the FcγRI (CD64), FcγRII (CD32), and FcγRIII (CD16) subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain.

(see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

As used herein, the term "antigen" is defined as any substance capable of eliciting an immune response. As used herein, the term "antigen specific" refers to a property of a cell population such that supply of a particular antigen, or a fragment of the antigen, results in specific cell proliferation.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or a T cell receptor.

As used herein, the term "specifically binding," refers to the interaction between binding pairs (e.g., an antibody and an antigen). In various instances, specifically binding can be embodied by an affinity constant of about 10-6 moles/liter, about 10-7 moles/liter, or about 10-8 moles/liter, or less.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816, 567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

Loop Kabat AbM Chothia Contact
L1 L24-L34 L24-L34 L26-L32 L30-L36
L2 L50-L56 L50-L56 L50-L52 L46-L55
L3 L89-L97 L89-L97 L91-L96 L89-L96
H1 H31-H35B H26-H35B H26-H32 H30-H35B
(Kabat Numbering)
H1 H31-H35 H26-H35 H26-H32 H30-H35
(Chothia Numbering)
H2 H50-H65 H50-H58 H53-H55 H47-H58
H3 H95-H102 H95-H102 H96-H101 H93-H101

Hypervariable regions may comprise "extended hypervariable regions" as follows: 24-36 or 24-34 (L1), 46-56 or 50-56 or 49-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" generally refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

As used herein, the term "antigen" is defined as any substance capable of eliciting an immune response.

As used herein, the term "antigen specific" refers to a property of a cell population such that supply of a particular antigen, or a fragment of the antigen, results in specific cell proliferation.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32, Pb212 and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran;

spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32, Pb212 and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

Administration "in combination with" one or more further therapeutic agents includes simultaneous (concurrent) and consecutive administration in any order.

Glycoantibodies

The glycosylation of recombinant proteins produced from mammalian cells in culture is an important process in ensuring the effective use of therapeutic antibodies (Goochee et al., 1991; Jenkins and Curling, 1994). Mammalian cell culture delivers a heterogeneous mixture of glycosylation patterns which do not all have the same properties. Properties like safety, efficacy and the serum half-life of therapeutic proteins can be affected by these glycosylation patterns. We have successfully addressed the glycoform heterogeneity problem by the development of a novel class of monoclonal antibodies, named "glycoantibodies".

The term "glycoantibodies" was coined by the inventor, Dr. Chi-Huey Wong, to refer to a homogeneous population of monoclonal antibodies (preferably, therapeutic monoclonal antibodies) having a single, uniformed glycoform on Fc. The individual glycoantibodies comprising the homogeneous population are identical, bind to the same epitope, and contain the same Fc glycan with a well-defined glycan structure and sequence.

Glycoantibodies may be generated from monoclonal antibodies (preferably, therapeutic monoclonal antibodies) commercially available or in the development. Monoclonal antibodies for therapeutic use can be humanized, human or chimeric. Examples of approved monoclonal antibodies for therapeutic use include, but not limited to, Muromomab, Abciximab, Rituximab, Daclizumab, Basiliximab, Palivizumab, Infliximab, Trastuzumab, Etanercept, Gemtuzumab, Alemtuzumab, Ibritomomab, Adalimumab, Alefacept, Omalizumab, Efalizumab, Cetuximab, Bevacizumab, Natalizumab, Ranibizumab, Panitumumab, Eculizumab and Certolizumab.

Described herein are the functionally active glycoantibodies derived from therapeutic monoclonal antibodies by Fc glycoengineering. The glycoantibodies with optimized glycoforms exhibit more potent biological activities compared to the therapeutic monoclonal antibodies. It is contemplated that the glycoantibodies with optimized glycoforms may provide an alternative for therapeutic use.

Anti-HER2 Glycoantibody (Anti-HER2 GAb)

The HER2 gene is overexpressed or amplified in approximately 30% of breast cancers. Breast cancer patients with HER2 overexpression or amplification have shortened disease-free and overall survivals. The HER2 protein is thought to be a unique and useful target for antibody therapy of cancers overexpressing the HER2 gene. A monoclonal antibody anti-HER2, Trastuzumab (Herceptin®), has been successfully used in therapy for malignant cancers relating to this target, which was approved by FDA in 1998 for the treatment of HER2 overexpressing breast cancer. A need remains for improved therapeutic antibodies against HER2 which are more effective in preventing and/or treating a range of diseases involving cells expressing HER2, including but not limited breast cancer.

The present disclosure features a novel class of anti-HER2 antibodies, termed "anti-HER2 glycoantibodies" ("anti-HER2 GAb"). The anti-HER2 glycoantibodies can be generated from anti-HER2 monoclonal antibodies by Fc glycoengineering. The individual anti-HER2 glycoantibodies comprising the homogeneous population are identical and contain the same Fc glycan with a well-defined glycan structure and sequence. The anti-HER2 GAb according to the present invention specifically binds to the same epitope of a human HER2 antigen as its patent antibody.

The term "parental antibody" as used herein refers to the anti-HER2 monoclonal antibody used to produce an anti-HER2 glycoantibody.

The parental antibodies can be obtained by cell culturing such as mammalian cell culture, *Pichia pastoris* or insect cell lines. Preferably, the parental antibodies are produced in mammalian cell culture. The parental antibodies may be FDA approved or in development. FDA approved anti-HER2 therapeutic antibodies include Trastuzumab (Herceptin), Lapatinib (Tykerb), Pertuzumab (Perjeta), Ado-trastuzumab emtansine (Kadcyla, Genentech).

In some embodiments, the anti-HER2 GAb described herein comprise a heavy chain having the amino acid sequence set forth in SEQ ID NO: 1, and a light chain having the amino acid sequence set forth in SEQ ID NO: 2. In a preferred embodiment, the anti-HER2 GAb comprises a light chain sequence and a heavy chain sequence of Trastuzumab.

Table 1 below shows the heavy chain and the light chain sequences of Trastuzumab.

TABLE 1

Table 1

Trastuzumab
Accession Number: DB00072
Source: http://www.drugbank.ca/drugs/DB00072
>Amino acid sequence for Trastuzumab light chain
DIQMTQSPSSLSASVGDRVTITCRASQDVNTAVAWYQQKPGKAPK
LLIYSASFLYSGVPSRFSGSRSGTDFTLTISSLQPEDFATYYCQQ
HYTTPPTFGQGTKVEIKRTVAAPSVFIFPPSDEQLKSGTASVVCL
LNNFYPREAKVQWKVDNALQSGNSQESVTEQDSKDSTYSLSSTLT
LSKADYEKHKVYACEVTHQGLSSPVTKSFNRGEC
(SEQ ID: 2)

>Amino acid sequence for Trastuzumab heavy chain
EVQLVESGGGLVQPGGSLRLSCAASGFNIKDTYIHWVRQAPGKGL
EWVARIYPTNGYTRYADSVKGRFTISADTSKNTAYLQMNSLRAED
TAVYYCSRWGGDGFYAMDYWGQGTLVTVSSASTKGPSVFPLAPSS
KSTSGGTAALGCLVKDYFPEPVTVSWNSGALTSGVHTFPAVLQSS
GLYSLSSVVTVPSSSLGTQTYICNVNHKPSNTKVDKKVEPKSCDK
THTCPPCPAPELLGGPSVFLFPPKPKDTLMISRTPEVTCVVVDVS
HEDPEVKFNWYVDGVEVHNAKTKPREEQYNSTYRVVSVLTVLHQD
WLNGKEYKCKVSNKALPAPIEKTISKAKGQPREPQVYTLPPSRE
EMTKNQVSLTCLVKGFYPSDIAVEWESNGQPENNYKTTPPVLDSDG
SFFLYSKLTVDKSRWQQGNVFSCSVMHEALHNHYTQKSLSLSPGK
(SEQ ID: 1)

In some embodiments, the N-glycan is attached to the Asn-297 of the Fc region.

The N-glycans according to the invention have a common pentasaccharide core of $Man_3GlcNAc_2$ which is also referred to as "trimannose core" or "pentasaccharide core", wherein "Man" refers to mannose, "Glc" refers to glucose, "NAc" refers to N-acetyl, and GlcNAc refers to N-acetylglucosamine.

In some embodiments, the N-glycan has a biantennary structure.

The N-glycan described herein may have intrachain substitutions comprising "bisecting" GlcNAc. When a glycan comprises a bisecting GlcNAc on the trimannose core, the structure is represented as Man$_3$GlcNAc$_3$. When a glycan comprises a core fucose attached to the trimannose core, the structure is represented as Man$_3$GlcNAc$_2$(F). The N-glycan may comprise one or more terminal sialic acids (e.g. N-acetylneuraminic acid). The structure represented as "Sia" refers to a terminal sialic acid. Sialylation may occur on either the α1-3 or α1-6 arm of the biantennary structures.

In some embodiments, the N-glycan described herein comprises at least one α2-6 terminal sialic acid. In certain embodiments, the N-glycan comprises one α2-6 terminal sialic acid. In a preferred embodiment, the N-glycan comprises two α2-6 terminal sialic acids.

In some embodiments, the N-glycan described herein comprises at least one α2-3 terminal sialic acid. In certain embodiments, the N-glycan comprises one α2-3 terminal sialic acid. In a preferred embodiment, the N-glycan comprises two α2-3 terminal sialic acids.

In some embodiments, the N-glycan described herein comprises at least one galactose. In certain embodiments, the N-glycan comprises one galactose. In a preferred embodiment, the N-glycan comprises two galactoses.

Preferably, the N-glycan according to the disclosure is free of core fucose.

Table 2 lists exemplary N-glycans of anti-HER2 glycoantibodies. Embodiments of the present disclosure may include or exclude any of the N-glycans listed herein.

TABLE 2

| GAb | Glycan structure | Glycan sequence |
|---|---|---|
| 101 | [biantennary structure with two Sia-Gal-GlcNAc-Man branches, α6 linkages] | Sia$_2$(α2-6)Gal$_2$GlcNAc$_2$Man$_3$GlcNAc$_2$ |
| 102 | [structure with one Sia on one branch] | Sia(α2-6)Gal$_2$GlcNAc$_2$Man$_3$GlcNAc$_2$ |
| 103 | [structure with one Sia-Gal branch] | Sia(α2-6)GalGlcNAc$_2$Man$_3$GlcNAc$_2$ |
| 104 | [biantennary with two Gal-GlcNAc branches] | Gal$_2$GlcNAc$_2$Man$_3$GlcNAc$_2$ |
| 105 | [structure with one Gal-GlcNAc branch] | GalGlcNAc$_2$Man$_3$GlcNAc$_2$ |
| 106 | [structure with one Gal-GlcNAc and one GlcNAc branch] | GalGlcNAcMan$_3$GlcNAc$_2$ |
| 107 | [structure with three GlcNAc] | GlcNAc$_3$Man$_3$GlcNAc$_2$ |

TABLE 2-continued

| GAb | Glycan structure | Glycan sequence |
|---|---|---|
| 108 | | GlcNAc$_2$Man$_3$GlcNAc$_2$ |
| 109 | | GlcNAcMan$_3$GlcNAc$_2$ |
| 110 | | GlcNAcMan$_3$GlcNAc$_2$ |
| 111 | | Man$_3$GlcNAc$_2$ |
| 112 | | Sia$_2$(α2-6)Gal$_2$GlcNAc$_3$Man$_3$GlcNAc$_2$ |
| 113 | | Sia(α2-6)Gal$_2$GlcNAc$_3$Man$_3$GlcNAc$_2$ |
| 114 | | Sia(α2-6)GalGlcNAc$_3$Man$_3$GlcNAc$_2$ |
| 115 | | Gal$_2$GlcNAc$_3$Man$_3$GlcNAc$_2$ |
| 116 | | GalGlcNAc$_3$Man$_3$GlcNAc$_2$ |
| 117 | | Sia$_2$(α2-3)Gal$_2$GlcNAc$_2$Man$_3$GlcNAc$_2$ |
| 118 | | Sia(α2-3)Gal$_2$GlcNAc$_2$Man$_3$GlcNAc$_2$ |

TABLE 2-continued

| GAb | Glycan structure | Glycan sequence |
|---|---|---|
| 119 | | Sia$_2$($\alpha$2-3)Gal$_2$GlcNAc$_3$Man$_3$GlcNAc$_2$ |
| 120 | | Sia($\alpha$2-3)Gal$_2$GlcNAc$_3$Man$_3$GlcNAc$_2$ |
| 121 | | Sia$_2$($\alpha$2-3/$\alpha$2-6) Gal$_2$GlcNAc$_3$Man$_3$GlcNAc$_2$ |
| 122 | | Sia$_2$($\alpha$2-6/$\alpha$2-3) Gal$_2$GlcNAc$_2$Man$_3$GlcNAc$_2$ |
| 123 | | Sia$_2$($\alpha$2-3/$\alpha$2-6) Gal$_2$GlcNAc$_3$Man$_3$GlcNAc$_2$ |
| 124 | | Sia$_2$($\alpha$2-6/$\alpha$2-3) Gal$_2$GlcNAc$_3$Man$_3$GlcNAc$_2$ |
| 125 | | Sia($\alpha$2-3)GalGlcNAc$_2$Man$_3$GlcNAc$_2$ |
| 126 | | Sia($\alpha$2-3)GalGlcNAc$_3$Man$_3$GlcNAc$_2$ |

Biological Characteristic of Anti-HER2 Glycoantibodies

Glycosylation on Fc can affect a variety of immunoglobulin effector-mediated functions, including ADCC, CDC and circulating half-life. ADCC enhancement is a key strategy for improving therapeutic antibody drug efficacy. It has the potential of lowering effective drug dosage for benefits of lower drug cost. The anti-HER2 glycoantibodies described herein can be characterized by functional properties. The anti-HER2 GAb has cell growth inhibitory activities including apoptosis against human HER2 expressing cells. In some embodiments, the anti-HER2 GAb exhibits more potent cell growth inhibitory activities as compared to its patent antibody.

ADCC Activities of Anti-HER2 Glycoantibodies

The ADCC activity of the glycoantibody according to the invention is at least 3 fold increased, preferably at least 9 fold, more preferably at least 10 fold increased ADCC activity, preferably at least 12 fold increased ADCC activity, preferably at least 20 fold increased ADCC activity, most preferred at least 30 fold increased ADCC activity compared to the ADCC activity of the parental antibody.

The ADCC lysis activity of the inventive glycoantibody can be measured in comparison to the parental antibody using target cancer cell lines such as SKBR5, SKBR3, LoVo, MCF7, OVCAR3 and/or Kato III.

Table 3 lists exemplary enhanced ADCC activities of anti-HER2 GAbs as compared to Trastuzumab. Exemplary assays are described in the examples.

TABLE 3

| Anti-HER2 | Trastuzumab | GAb101 | GAb104 | GAb105 | GAb107 | GAb108 | GAb111 |
|---|---|---|---|---|---|---|---|
| ADCC (fold) | 1 | >30 | >30 | 20~30 | >10 | 5~10 | 1~5 |

A number of anti-HER2 GAbs described herein, in particular GAb101, and GAb104, exhibit enhanced ADCC activity compared to it parental antibody, Trastuzumab. It is contemplated that the glycoantibodies of the invention may exhibit superior effect as therapeutic agents for HER2-positive diseases, and an object of the present invention is to use the anti-HER2 GAb in development of therapeutic agents.

CDC Activities of Anti-HER2 Glycoantibodies

The glycoantibody described herein is surprisingly able to provide improved ADCC without affecting CDC. Exemplary CDC assays are described in the examples. In exemplary embodiments, ADCC of the glycoantibody is increased but other immunoglobulin-type effector functions such as complement-dependent cytoxicity (CDC) remain similar or are not significantly affected.

Binding Between FcγRIII and Anti-HER2 Glycoantibodies

Table 4 lists exemplary FcγRIIIA binding of anti-HER2 GAbs and Herceptin.

TABLE 4

| Sample | KD (M) | Rmax (RU) | Fold |
|---|---|---|---|
| Herceptin | 80~200 | 30.01 | 1-fold |
| 101 | 1~25 | 44.98 | >10X |
| 104 | 1~25 | 55.68 | >10X |
| 111 | 35~100 | 41.54 | 1~5X |
| 108 | 25~100 | 53.98 | 1~5X |
| 107 | 20~90 | 39.88 | 3~10X |
| 109 | 25~80 | 48.19 | 2~10X |
| 110 | 70~150 | 18.15 | 1~5X |
| 106 | 25~80 | 52.82 | 1~10X |
| 103 | 15~70 | 59.89 | 4~10X |
| 117 | 1~50 | 26.95 | 1~5X |

FcγRIIIA binding may be measured using assays known in the art. Exemplary assays are described in the examples. The Fc receptor binding may be determined as the relative ratio of anti-HER2 GAb vs Trastuzumab. Fc receptor binding in exemplary embodiments is increased by at least 2.5-fold, 3-fold, 4-fold, 5-fold, 6-fold, 7-fold, 8-fold, 9-fold, 10-fold, 11-fold or 20-fold, 30-fold, 40-fold, 50-fold or higher.

As compared to Trastuzumab, the binding data showed that the anti-HER2 GAbs, in particular GAb101 and GAb104, exhibit stronger binding affinity for the target molecule HER2.

Taken together, anti-HER2 GAbs, in particular GAb101, and GAb104, exhibit enhanced ADCC activity and stronger FcγRIIIA binding affinity as compared to Trastuzumab. It is contemplated that the glycoantibodies of the invention may provide a superior clinical response either alone or, preferably, in a composition comprising two or more such antibodies, and optionally in combination with other treatments such as chemotherapy. It is contemplated that the ADCC-enhanced anti-HER2 glycoantibody may provide an alternative therapeutic for HER2-positive diseases. The glycoantibodies of the present invention advantageously can be used to alter current routes of administration and current therapeutic regimens, as their increased effector function means they can be dosed at lower concentrations and with less frequency, thereby reducing the potential for antibody toxicity and/or development of antibody tolerance. Furthermore, their improved effector function yields new approaches to treating clinical indications that have previously been resistant or refractory to treatment with the corresponding anti-HER2 monoclonal antibody produced in recombinant host systems.

Preparation of Anti-HER2 GAb

The anti-HER2 glycoantibodies of the invention can be produced by Fc glycoengineering from anti-HER2 monoclonal antibodies ("parental antibodies") commercially available or in the preclinical or clinical development. Preferably, the monoclonal antibodies are therapeutic monoclonal antibodies. Fc glycoengineering may be performed enzymatically or chemoenzymatically. In a preferred embodiment, the parental antibody is Trastuzumab.

The N-glycans in the glycoantibodies of the invention are preferably defucosylated.

Defucosylation of N-glycans is a process to remove core fucoses in N-glycans of the Fc domains. Defucosylation can be employed enzymatically. Since N-glycans are embedded between two Fc domains, the enzymatic defucosylation efficiency is much lower due to steric hindrance, i.e., access of fucosidase to fucose residues is blocked by potions of the Fc domains.

Many α-fucosidases are known in the art. Examples include α-fucosidases from *Turbo cornutus, Charonia lampas, Bacillus fulminans, Aspergillus niger, Clostridium perfringens*, Bovine kidney (Glyko), chicken liver (Tyagarajan et al., 1996, Glycobiology 6:83-93) and α-fucosidase II from *Xanthomonas manihotis* (Glyko, PROzyme). Many varieties of fucosidase are also commercially available (Glyko, Novato, Calif.; PROzyme, San Leandro, Calif.; Calbiochem-Novabiochem Corp., San Diego, Calif.; among others). However, none of α-fucosidases are known to efficiently remove the core fucose from N-linked glycans.

WO 2013/12066 disclosed the defucosylation of (Fucα1, 6)GlcNAc-Rituximab by an α-fucosidase from bovine kidney. As described in WO 2013/12066, a reaction mixture of (Fucα1, 6)GlcNAc-Rituximab was incubated with α-fucosidase from bovine kidney (commercially available from Prozyme) at 37° C. for 20 days to completely remove the fucose in (Fucα1, 6)GlcNAc-Rituximab.

Thermal instability of immunoglobulin is known in the art (Vermeer et al., Biophys J. January 78: 394-404 (2000)). The Fab fragment is most sensitive to heat treatment, whereas the Fc fragment is most sensitive to decreasing pH. To examine the thermal stability and functional activity of the antibody, we performed the same experiment as described in WO 2013/12066, and found the antibody lost about 10% binding affinity to CD20 after thermal treatment at 37° C. for 3 days. Furthermore, we found the antibody lost about 20% binding affinity to CD20 after thermal treatment at 37° C. for 7 days.

It is contemplated that the antibody will significantly lose the binding affinity to CD20 after prolonged thermal treatment, such as at 37° C. for 20 days, as described in WO 2013/12066.

In our attempts to synthesize the glycoantibodies with improved therapeutic values, we unexpectedly discovered a *Bacteroides fragilis* α-fucosidase (GenBank accession no. YP_212855.1) that is capable of efficiently removing fucose residues from N-linked glycans. Efficient defucosylation has been successfully achieved using the specific enzyme. Importantly, the efficiency of making the glycoantibodies of the invention has been valuably improved by the use of the specific α-fucosidase that yields a facile defucosylation of N-glycans, as illustrated in FIG. 1.

Accordingly, the present invention provides a composition of the α-fucosidase, and an improved method for removing core fucoses of N-glycans using the α-fucosidase. The α-fucosidase comprises a polypeptide having an amino acid sequence having at least 80%, 85% 90%, 95%, 98% or 99% identity to the sequences of SEQ ID NO: 5 or variants thereof. The improved method of defucosylation comprises contacting an antibody with an α-fucosidase, and in which the α-fucosidase comprises a polypeptide having an amino acid sequence having at least 80%, 85%, 90%, 95%, 98% or 99% identity to the sequences of SEQ ID NO: 5, a variant or a fragment thereof.

Described herein includes an improved method for making an anti-HER2 glycoantibody, the method comprising the steps of (a) contacting an anti-HER2 monoclonal antibody with an α-fucosidase and at least one endoglycosidase, thereby yielding a defucosylated antibody having a single N-acetylglucosamine (GlcNAc), and (b) adding a carbohydrate moiety to GlcNAc under suitable conditions.

In some embodiments, the anti-HER2 monoclonal antibody is Trastuzumab.

Endoglycosidase is used to trim off the variable portions of an oligosaccharide in N-glycan. Examples of endoglycosidases used herein include, but not limited to, EndoA, EndoF, EndoF1, EndoF2, EndoH, EndoM, EndoS, and variants thereof.

The α-fucosidase according to the method of the invention comprises a polypeptide having an amino acid sequence having at least 85% identity to the sequences of SEQ ID NO: 5, a functional variant thereof.

In some embodiments, the α-fucosidase comprises a polypeptide having an amino acid sequence having at least 90%, 91%, 92%, 93%, 94%, 95%, 96%, 97%, 98%, 99% identity to the sequences of SEQ ID NO: 5, a variant or a fragment thereof.

In certain embodiments, the α-fucosidase is a recombinant *Bacteroides* α-fucosidase.

TABLE 5

```
QQKYQPTEANLKARSEFQDNKFGIFLHWGLYAMLATGEWT
MTNNNLNYKEYAKLAGGFYPSKFDADKWVAAIKASGAKYI
CFTTRHHEGFSMFDTKYSDYNIVKATPFKRDVVKELADAC
AKHGIKLHFYYSHIDWYREDAPQGRTGRRTGRPNPKGDWK
SYYQFMNNQLTELLTNYGPIGAIWFDGWWDQDINPDFDWE
LPEQYALIHRLQPACLVGNNHHQTPFAGEDIQIFERDLPG
ENTAGLSGQSVSHLPLETCETMNGMWGYKITDQNYKSTKT
LIHYLVKAAGKDANLLMNIGPQPDGELPEVAVQRLKEVGE
WMSKYGETIYGTRGGLVAPHDWGVTTQKGNKLYVHILNLQ
DKALFLPIVDKKVKKAVVFADKTPVRFTKNKEGIVLELAK
VPTDVDYVVELTID
(SEQ ID: 5)
```

Step (a) in the method of the invention leads to a defucosylated antibody having a single N-acetylglucosamine (GlcNAc). Subsequent enzyme-mediated glycosylation using a transglycosylase is performed to add a designated carbohydrate moiety to GlcNAc and extend the sugar chain. A homogenous population of glycoantibodies can therefore be produced. Examples of transglycosylases as described herein include, but not limited to, EndoA, EndoF, EndoF1, EndoF2, EndoH, EndoM, EndoS, and variants thereof.

In some embodiments, the carbohydrate moiety according to the method the invention is selected from the group consisting of

| Carbohydrate | Sialic acid |
|---|---|
| $Sia_2(\alpha2\text{-}6)Gal_2GlcNAc_2Man_3GlcNAc$, | |
| $Sia_2(\alpha2\text{-}6)Gal_2GlcNAc_3Man_3GlcNAc$, | $Sia_2(\alpha2\text{-}3)$ |
| $Gal_2GlcNAc_2Man_3GlcNAc$, | $Sia_2(\alpha2\text{-}3)$ |
| $Gal_2GlcNAc_3Man_3GlcNAc$, | $Sia_2(\alpha2\text{-}3/\alpha2\text{-}6)$ |
| $Gal_2GlcNAc_2Man_3GlcNAc$, | $Sia_2(\alpha2\text{-}6/\alpha2\text{-}3)$ |
| $Gal_2GlcNAc_2Man_3GlcNAc$, | $Sia_2(\alpha2\text{-}3/\alpha2\text{-}6)$ |
| $Gal_2GlcNAc_3Man_3GlcNAc$, | $Sia_2(\alpha2\text{-}6/\alpha2\text{-}3)$ |
| $Gal_2GlcNAc_3Man_3GlcNAc$, | $Sia(\alpha2\text{-}6)$ |
| $Gal_2GlcNAc_2Man_3GlcNAc$, | $Sia(\alpha2\text{-}3)$ |
| $Gal_2GlcNAc_2Man_3GlcNAc$, | $Sia(\alpha2\text{-}6)$ |
| $Gal_2GlcNAc_3Man_3GlcNAc$, | $Sia(\alpha2\text{-}3)$ |
| $Gal_2GlcNAc_3Man_3GlcNAc$, | $Sia(\alpha2\text{-}6)$ |
| $GalGlcNAc_2Man_3GlcNAc$, | $Sia(\alpha2\text{-}3)$ |
| $GalGlcNAc_2Man_3GlcNAc$, | $Sia(\alpha2\text{-}6)$ |
| $GalGlcNAc_3Man_3GlcNAc$, | $Sia(\alpha2\text{-}3)$ |
| $GalGlcNAc_3Man_3GlcNAc$, | $Gal_2GlcNAc_2Man_3GlcNAc$, |
| $Gal_2GlcNAc_3Man_3GlcNAc$, | $GalGlcNAc_2Man_3GlcNAc$, |
| $GalGlcNAc_3Man_3GlcNAc$, | $GlcNAc_3Man_3GlcNAc$, |
| $GlcNAc_2Man_3GlcNAc$, | $GlcNAcMan_3GlcNAc$ and $Man_3GlcNAc$. |

In preferred embodiments, the carbohydrate moiety is selected from the group consisting of

| Carbohydrate | Sialic acid |
|---|---|
| | $Sia_2(\alpha2\text{-}6)$ |
| $Gal_2GlcNAc_2Man_3GlcNAc$, | $Sia_2(\alpha2\text{-}6)$ |
| $Gal_2GlcNAc_3Man_3GlcNAc$, | $Sia_2(\alpha2\text{-}3)$ |
| $Gal_2GlcNAc_2Man_3GlcNAc$, | $Sia_2(\alpha2\text{-}3)$ |
| $Gal_2GlcNAc_3Man_3GlcNAc$, | $Sia_2(\alpha2\text{-}3/\alpha2\text{-}6)$ |
| $Gal_2GlcNAc_2Man_3GlcNAc$, | $Sia_2(\alpha2\text{-}6/\alpha2\text{-}3)$ |
| $Gal_2GlcNAc_2Man_3GlcNAc$, | $Sia_2(\alpha2\text{-}3/\alpha2\text{-}6)$ |
| $Gal_2GlcNAc_3Man_3GlcNAc$, | $Sia_2(\alpha2\text{-}6/\alpha2\text{-}3)$ |
| $Gal_2GlcNAc_3Man_3GlcNAc$, | $Sia(\alpha2\text{-}6)$ |
| $Gal_2GlcNAc_2Man_3GlcNAc$, | $Sia(\alpha2\text{-}3)$ |
| $Gal_2GlcNAc_2Man_3GlcNAc$, | $Sia(\alpha2\text{-}6)$ |
| $Gal_2GlcNAc_3Man_3GlcNAc$, | $Sia(\alpha2\text{-}3)$ |
| $Gal_2GlcNAc_3Man_3GlcNAc$, | $Sia(\alpha2\text{-}6)$ |
| $GalGlcNAc_2Man_3GlcNAc$, | $Sia(\alpha2\text{-}3)$ |
| $GalGlcNAc_2Man_3GlcNAc$, | $Sia(\alpha2\text{-}6)$ |
| $GalGlcNAc_3Man_3GlcNAc$, | $Sia(\alpha2\text{-}3)$ |
| $GalGlcNAc_3Man_3GlcNAc$, $Gal_2GlcNAc_2Man_3GlcNAc$ and $Gal_2GlcNAc_3Man_3GlcNAc$. | |

Step (b) in the method of the invention leads to sugar chain extension. One method for sugar chain extension is through an enzyme-catalyzed glycosylation reaction. It is well known in the art that glycosylation using a sugar oxazoline as the sugar donor among the enzyme-catalyzed glycosylation reactions is useful for synthesizing oligosaccharides because the glycosylation reaction is an addition reaction and advances without any accompanying elimination of acid, water, or the like. (Fujita, et al., *Biochim. Biophys. Acta* 2001, 1528, 9-14)

In some embodiments, the carbohydrate moiety is a sugar oxazoline.

Suitable conditions also include incubation of the reaction mixture for at least 20 minutes, 30 minutes, 40 minutes, 50 minutes, 60 minutes, 70 minutes, 80 minutes, 90 minutes or 100 minutes, preferably less than 60 minutes. Incubation preferably takes place at room temperature, more preferably at approximately 20° C., 25° C., 30° C., 35° C., 40° C. or 45° C., and most preferably at approximately 37° C.

It will be understood that the polypeptide of the α-fucosidase of the invention may be derivatized or modified to assist with their isolation or purification. Thus, in one embodiment of the invention, the polypeptide for use in the invention is derivatized or modified by addition of a ligand which is capable of binding directly and specifically to a separation means. Alternatively, the polypeptide is derivatized or modified by addition of one member of a binding pair and the separation means comprises a reagent that is derivatized or modified by addition of the other member of a binding pair. Any suitable binding pair can be used. In a preferred embodiment where the polypeptide for use in the invention is derivatized or modified by addition of one member of a binding pair, the polypeptide is preferably histidine-tagged or biotin-tagged. Typically the amino acid coding sequence of the histidine or biotin tag is included at the gene level and the proteins are expressed recombinantly in E. coli. The histidine or biotin tag is typically present at one end of the polypeptide, either at the N-terminus or at the C-terminus. The histidine tag typically consists of six histidine residues (SEQ ID NO: 6), although it can be longer than this, typically up to 7, 8, 9, 10 or 20 amino acids or shorter, for example 5, 4, 3, 2 or 1 amino acids. Furthermore, the histidine tag may contain one or more amino acid substitutions, preferably conservative substitutions as defined above.

Variant polypeptide as described herein are those for which the amino acid sequence varies from that in SEQ ID NO: 5, but exhibit the same or similar function of the enzyme comprising the polypeptide having an amino acid sequence of SEQ ID NO: 5.

As used herein percent (%) sequence identity with respect to a sequence is defined as the percentage of amino acid residues in a candidate polypeptide sequence that are identical with the amino acid residues in the reference polypeptide sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared.

Some preferred embodiments of the invention are demonstrated in the examples.

Pharmaceutical Compositions and Formulations

After preparation of the anti-HER2 GAb as described herein, a "pre-lyophilized formulation" can be produced. The anti-HER2 GAb for preparing the formulation is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition. In certain embodiments, the protein is an antibody.

The amount of anti-HER2 GAb in the pre-lyophilized formulation is determined taking into account the desired dose volumes, mode(s) of administration etc. Where the protein of choice is an intact antibody (a full-length antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable. A "stable" formulation/composition is one in which the antibody therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 μm size.

Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Antibody Derivatives

Antibodies of the invention can be further modified to contain additional nonproteinaceous moieties that are known in the art and readily available. In one embodiment, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, the polymers can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Therapeutic Applications

Trastuzumab (Herceptin®) is widely used and known in the art for the treatment of patients with early as well as metastatic breast cancer whose tumors overexpress HER2 protein or have HER 2 gene amplification. In the art, the treatment of breast cancer patients with Herceptin/Trastuzumab is, for example, recommended and routine for patients having HER2-positive disease. HER2-positive disease in breast cancer is present if a high HER2 (protein) expression level detected by immunohistochemical methods (e.g. HER2 (+++) or HER2 gene amplification (e.g. a HER2 gene copy number higher than 4 copies of the HER2 gene per tumor cell) or both is found in samples obtained from the patients such as breast tissue biopsies or breast tissue resections or in tissue derived from metastatic sites.

ADCC-enhanced anti-HER2 glycoantibodies provides an alternative therapeutic for treating HER2-expressing tumors. The glycoantibodies of the present invention advantageously can be used to alter current routes of administration and current therapeutic regimens, as their increased effector function means they can be dosed at lower concentrations and with less frequency, thereby reducing the potential for antibody toxicity and/or development of antibody tolerance. Furthermore, their improved effector function yields new approaches to treating clinical indications that have previously been resistant or refractory to treatment with the corresponding anti-HER2 monoclonal antibody produced in recombinant host systems.

Accordingly, the present disclosure relates to a method for treating a patient having a HER2-expressing tumor comprising administering to the patient an effective amount of the glycoantibody described herein. In a preferred aspect, the present disclosure provides a method for treating breast cancer.

The composition described above can be a pharmaceutical composition, which can further comprise a pharmaceutically acceptable carrier.

The composition can be delivered by administering the composition to a subject in need thereof (e.g., a human patient having or suspected of having cancer). In some embodiments, the anti-cancer agent is delivered to a subject in an amount effective in treating cancer. In other embodiments, a detectable label, preferably an agent suitable for cancer imaging, is delivered to a subject (e.g., a human patient having or suspected of having a solid tumor) in an amount effective in detecting cancer cells and/or cancerous tissues.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC);

phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., Proc. Natl. Acad. Sci. (USA) 95:652-656 (1998).

"Fc receptor" or "FcR" describes a receptor that binds to the Fe region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (reviewed by M. Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen, To assess complement activation, a CDC assay, e.g., as described in Gazzano-Santoro et al., J. Immunol. Methods 202:163 (1996), may be performed.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal See preceding definition of "treating."

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The details of one or more embodiments of the invention are set forth in the description below. Other features or advantages of the present invention will be apparent from the following drawings and detailed description of several embodiments, and also from the appending claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Exemplary General Procedures
Method A: Glycosylation by Thio-Glycan Donor

To activate molecular sieves MS-4 Å for glycosylation, it was connected to vacuum system and heated for 1 hour. After the activated molecular sieves was cooled to room temperature, it was added to a flask containing Donor (1.5~2.0 eq. for one position glycosylation) and Acceptor (1.0 eq.). Dichloromethane was added to the mixture, and then the solution was stirred at room temperature for 3 h. N-iodosuccinimide (NIS, 1.7~2.2 eq.) and trimethylsilyl trifluoromethanesulfonate (TMSOTf, 0.1 eq.) were added to the solution on −78° C., and then the solution was stirred at −20° C. Reaction was monitored by thin-layer chromatography (TLC) analysis, which was carried out on glass-backed silica gel plates (Merck DC Kieselgel 60F$_{254}$) and visualized by UV light (254 nm) and acidic ceric ammonium molybdate. After the acceptor was consumed completely, the reaction was quenched with sat. NaHCO$_{3(aq)}$, and 20% Na$_2$S$_2$O$_3$, and then the mixture was filtered through a pad of celite. After the aqueous layer was extracted with two portions of dichloromethane, the combined organic layers were washed with brine, dried over MgSO$_4$, and concentrated. The crude was purified by silica gel column chromatography (toluene/ethyl acetate as elution system) to give product (the yield was shown on the scheme).

Method B: Glycosylation by Fluoride-Glycan Donor

A mixture of silver triflate (5 eq.), bis(cyclopentadienyl) hafnium dichloride (3.5 eq.) and 4 Å activated molecular sieves in dry toluene was stirred at room temperature for 1 h. The reaction mixture was then cooled to −50° C., a solution of acceptor (1.0 eq.) and donor (1.2~1.5 eq.) in toluene was added. The mixture was stirred at −10° C. for 2-8 h. After TLC indicated complete consumption of acceptor, the reaction was quenched with Et$_3$N, diluted with EtOAc and filtered through Celite. The filtrate was washed with aqueous NaHCO$_3$, and a brine solution. The organic layers was dried over Na$_2$SO$_4$ and concentrated in vacuo. The crude was purified by silica gel column chromatography (toluene/ethyl acetate as elution system) to give product (the yield was shown on the scheme).

Method C: Deprotection of O-Acetyl

NaOMe (0.25 eq.) was added to solution of starting material (1.0 eq.) in THF/Methanol (2/3). Reaction was stirred at room temperature and monitored by TLC analysis. After the acetyl group was de-protected completely, the solution was neutralized by IR-120, filtered, and concentrated. The crude was purified by silica gel column chromatography (hexanes/ethyl acetate as elution system) to give product (the yield was shown on the scheme).

Method D: Deprotection of O-Troc

Zn powder (20 eq.) and acetic acid (0.2 eq.) were added to solution of starting material (1.0 eq.) in THF. Reaction was stirred at room temperature and monitored by thin-layer chromatography (TLC) analysis. After the Troc group was de-protected completely, the solution was filtered, and concentrated. The crude was purified by silica gel column chromatography (hexanes/ethyl acetate as elution system) to give product (the yield was shown on the scheme).

Method E: Deprotection of Benzylidene p-Toluenesulfonic acid (pTSA, 1.5 eq.) was added to solution of starting material (1.0 eq.) in ACN/MeOH (2/1). Reaction was stirred at room temperature and monitored by thin-layer chromatography (TLC) analysis. After the benzylidene group was removed completely, the reaction was quenched by trimethylamine and then concentrated. The crude was purified by silica gel column chromatography (hexanes/ethyl acetate as elution system) to give product (the yield was shown on the scheme).

Method F: Global Deprotection

A mixture of protected oligosaccharides (50 mmol) and 10 mL of ethylene diamine: nBuOH (1/4) were stirred at 90° C. overnight. Volatiles were evaporated, and crude was reacted with 10 mL Ac$_2$O/pyridine (1/2) overnight. The solvents were removed using high vacuum, and the product was purified by flash column chromatography (acetone/toluene as elute system). The products were de-acetylated using sodium methoxide in MeOH (10 mL) overnight. Reactions were neutralized by using IR-120, then, filtered and concentrated in vacuum. The residues were purified by flash column chromatography (acetone/toluene as elute system). The products were dissolved in 10 mL MeOH:H$_2$O: HCOOH (6/3/1), Pd(OH)$_2$ (50% by weight) was added, and the reactions were hydrogenated overnight. The reaction mixtures were filtered through celite and concentrated in vacuo. The residues were purified by G-15 gel column chromatography using water as eluent. The products were lypholysed to get white color powders (the yield was shown on the scheme).

Method G: Enzymatic (2,6)-Sialylation

Starting materials (5 μmol), CTP (1 μmol), Neu5Ac (9.5 μmol), PEP (10 μmol), □-2,6 sialyltransferase (200 μL, estimated concentration of 2 mg/L), CMK (80 units), PK (40 units), and PPA (40 units) were dissolved in 50 μmol sodium cacodylate (pH 7.4) containing 1% BSA (130 μL). The reactions were incubated at 37° C. with gentle agitation for 2d. The products were purified by using G-15 gel chromatography (eluent H$_2$O) to afford the desired products as white solid after lyophilization.

Building Blocks:

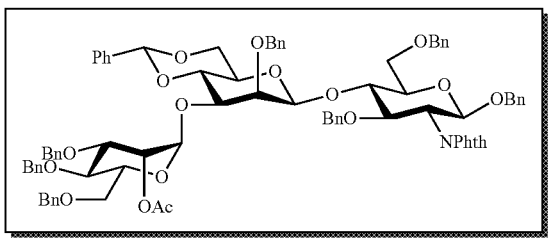

A

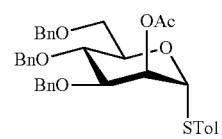

B

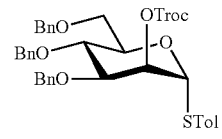

C

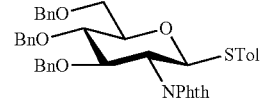

D

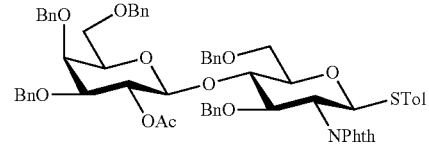

E

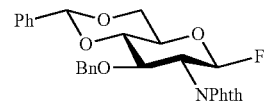

F

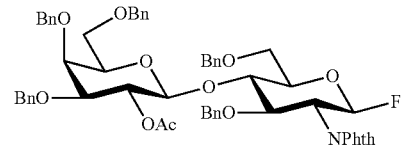

G

Experimental Procedures for Synthesizing Asymmetric N-Glycans

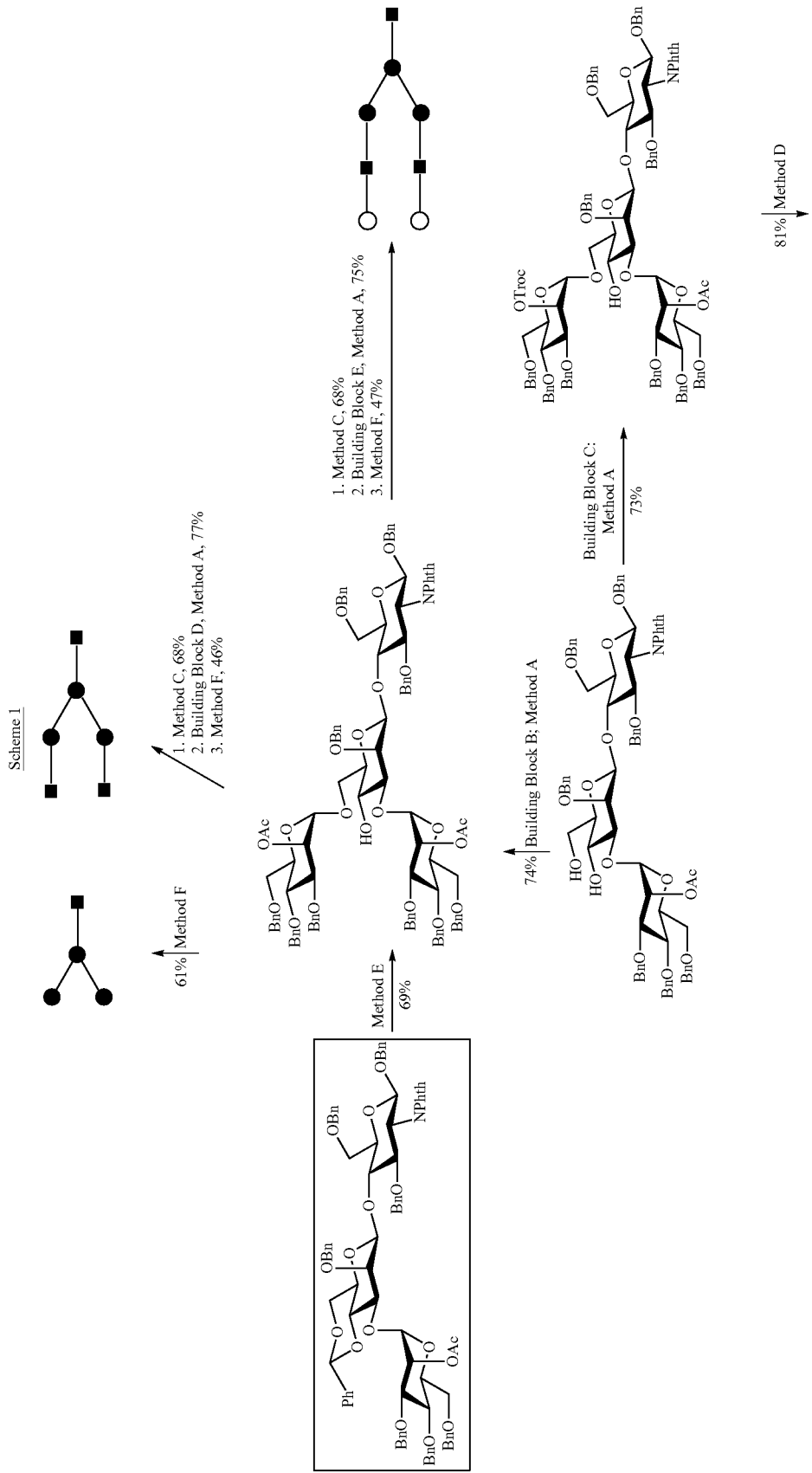
Scheme 1

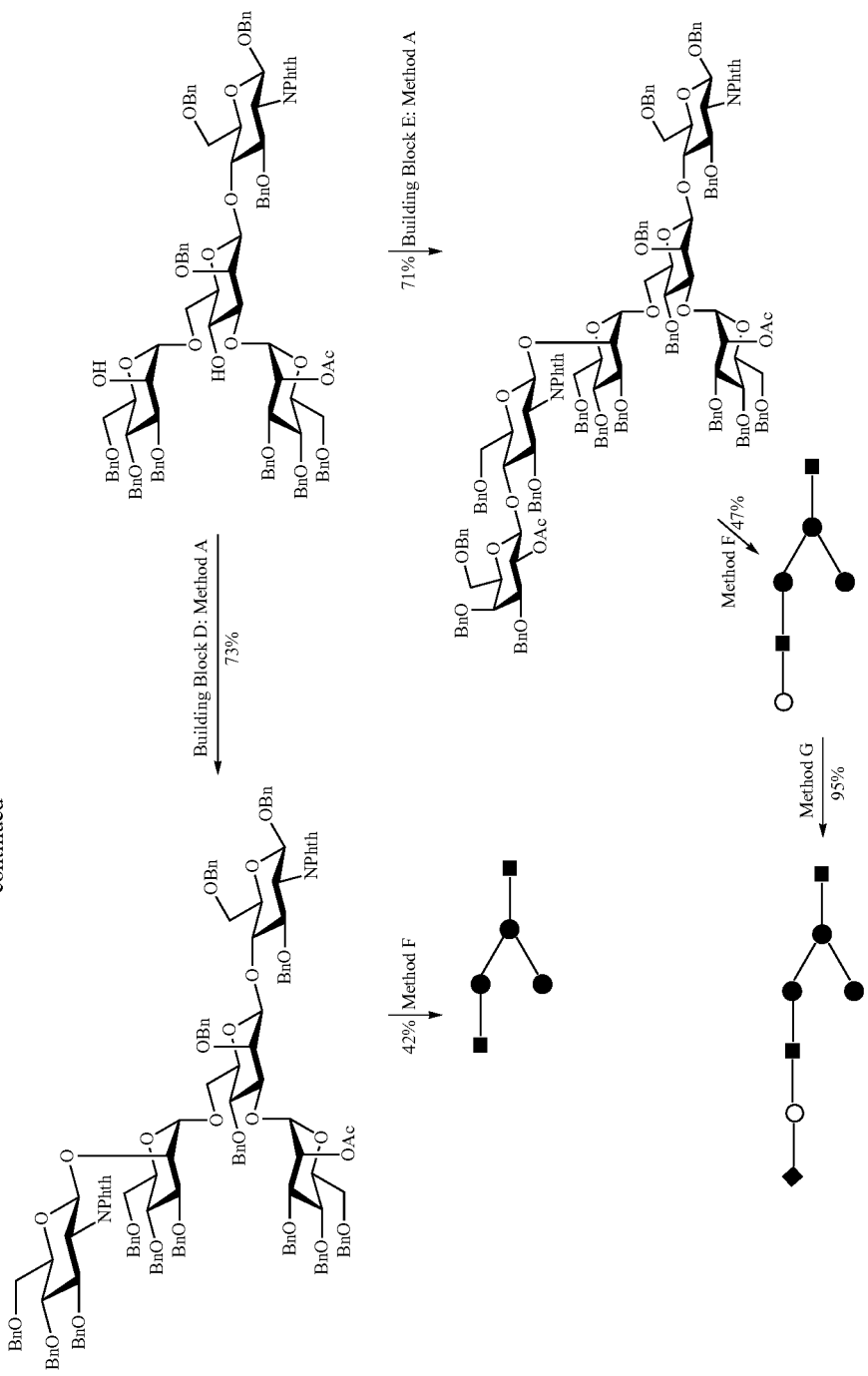

Experimental Procedures for Synthesizing Asymmetric N-Glycans

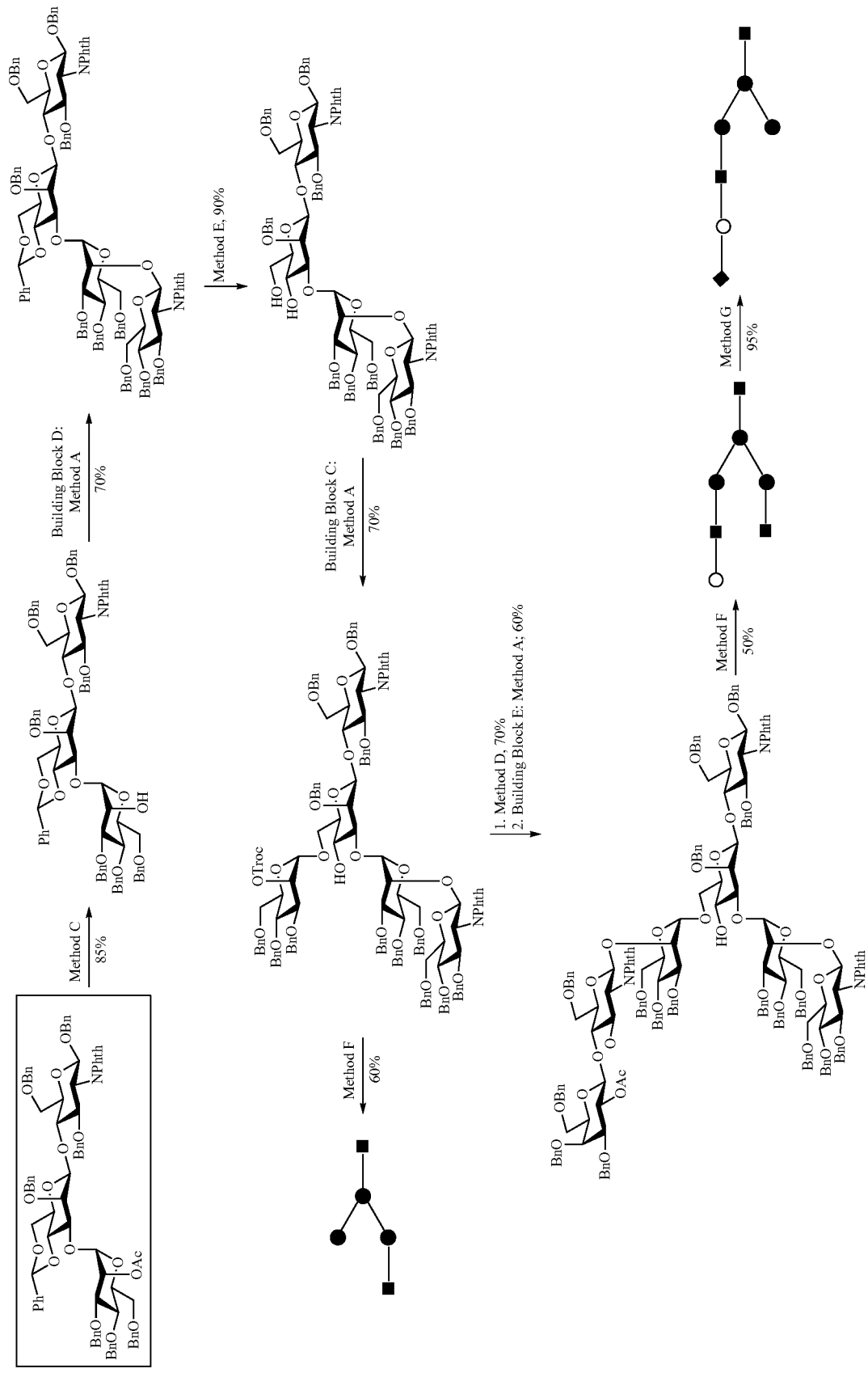

Experimental Procedures for Synthesizing Asymmetric N-Glycans

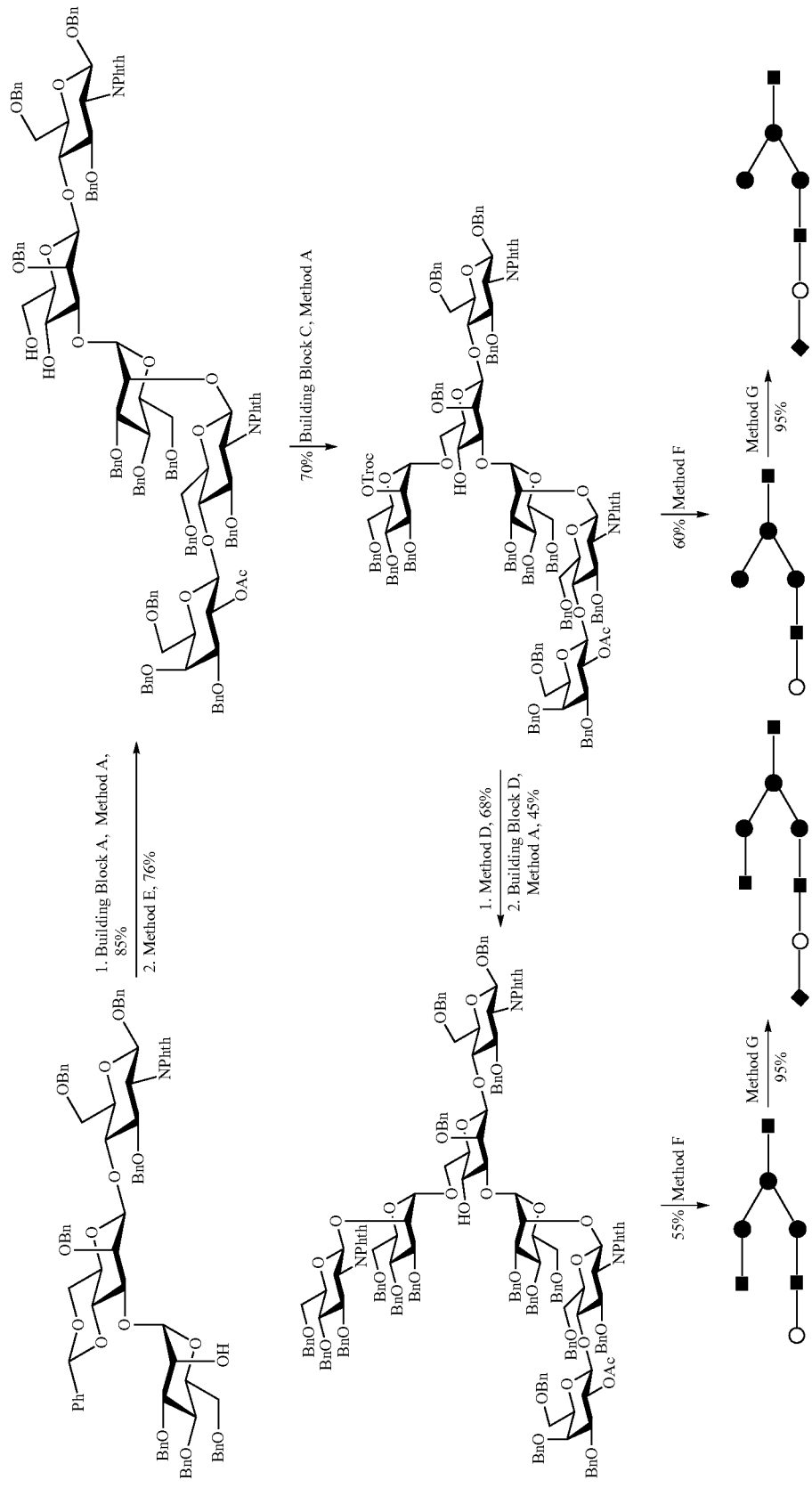

Experimental Procedures for Synthesizing Asymmetric N-Glycans
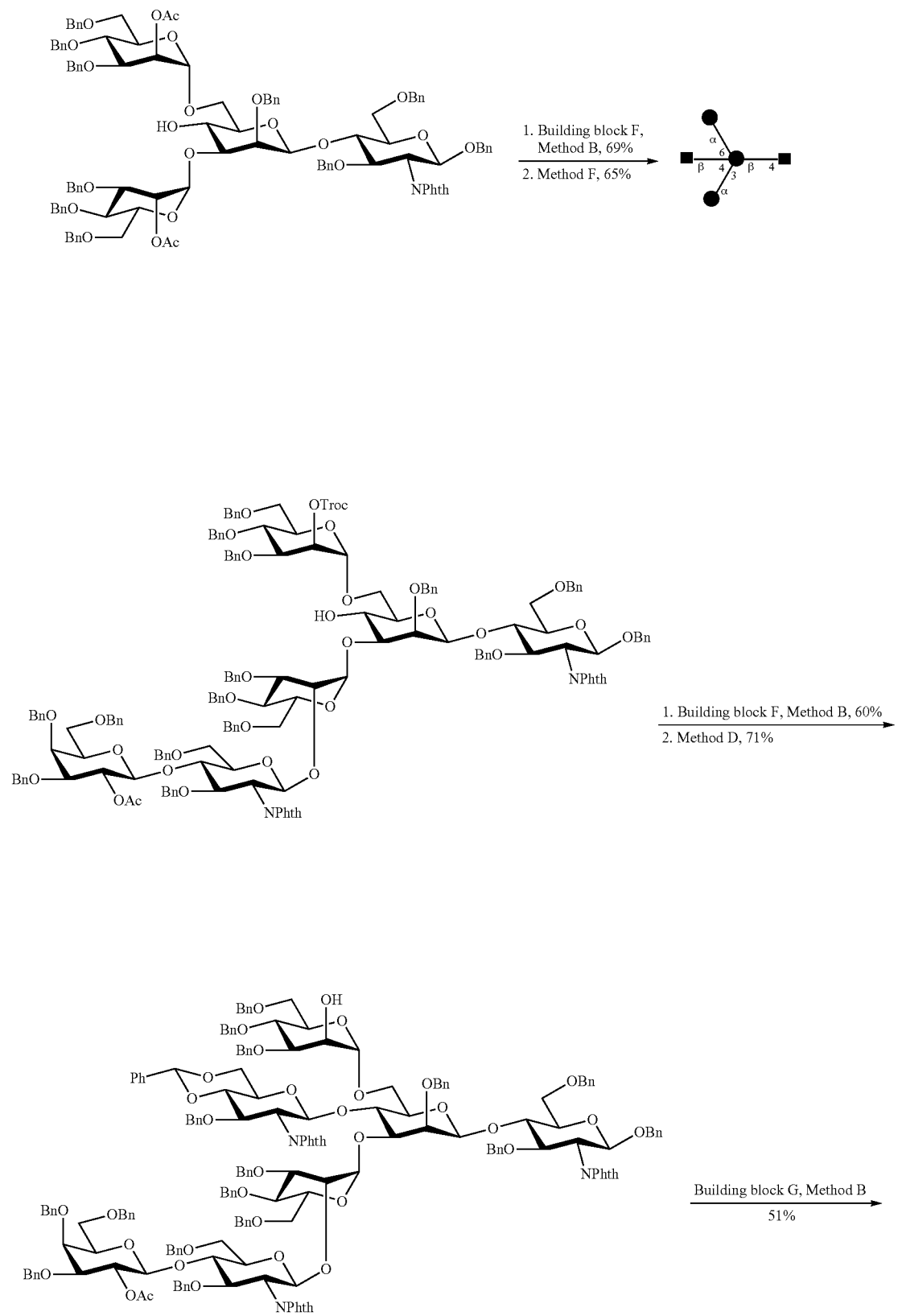
Scheme 4

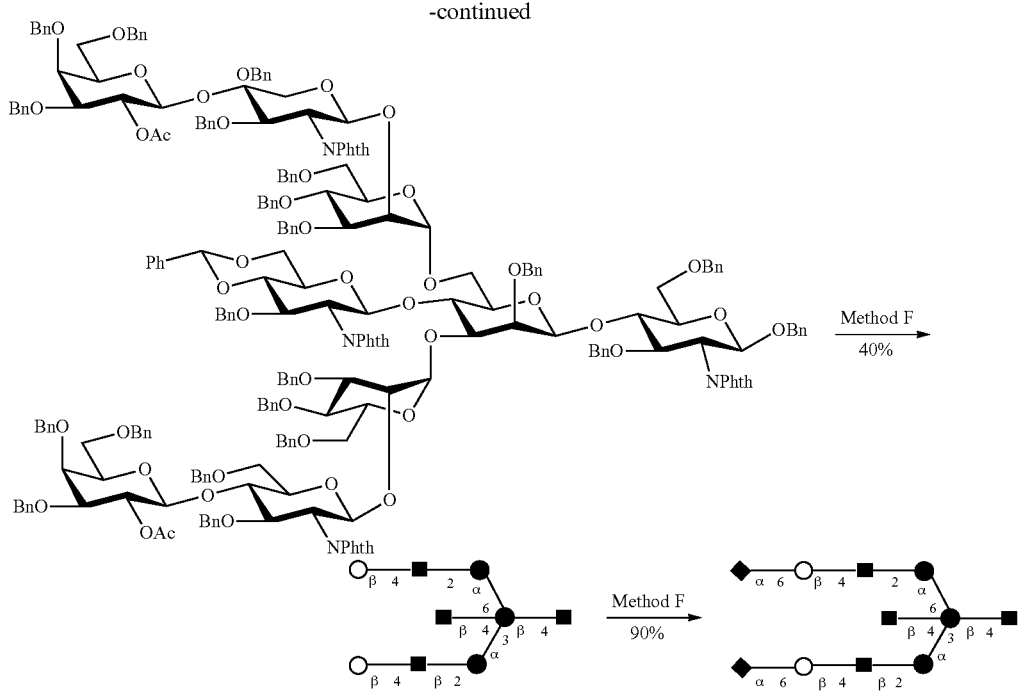

Example 1

Generation of Exemplary Anti-HER2 GAbs

Anti-HER2 GAb301

The complete removal of N-linked glycan at $Asn^{297}$ from Fc region of Trastuzumab (Herceptin) is achieved by means of PNGase F, and evaluated with 4-12% Bis-Tris NeuPAGE and LC-MS/MS analysis of tryptic glycopeptides from modified and unmodified IgG. The molecular weights of tryptic glycopeptides helps to determine the potential site of N-linked glycosylation at each asparagine and to elucidate the species of predominant glycans.

Anti-HER2 GAb201

A glycoantibody derived from conventional Trastuzumab (Herceptin) bearing a glycan structure of GlcNAc-Fuc in the Fc region was treated with one or more endoglycosidases (Endo S and/or Endo F1, Endo F2, Endo F3), and then treated with an alpha-fucosidase to cleave the core fucose with a high cleavage efficiency and lead to a glycoantibody with a monosaccharide GlcNAc in the Fc region.

Mixtures of Endo S (10 μg), Endo F1/Endo F2/Endo F3 (10 μg), Fucosidase (2 mg) and Trastuzumab (2 mg) in 50 mM sodium phosphate buffer (pH 7) were shaking at 37° C. for 24 hr. The reaction mixture was subjected to protein A affinity column for purification. The fraction of anti-HER2 GAb201 was collected (yield: 96.6%). The collected fraction was trypsinized. The trypsinized glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb201.

Anti-HER2 GAb101

Ethanol was added into 100 mL of chicken egg yolk and mixed thoroughly. After centrifugation, the supernatant was discarded and the pellet was collected. The pellet was washed twice with ethanol. Water was added into the pellet and mixed thoroughly. The mixture was centrifuged. After centrifugation, the supernatant was discarded and the pellet was collected. The pellet was mixed with ethanol. A supernatant was collected and lyophilized to obtain 1.5 g white de-fat powder. The powder was dissolved in phosphate buffer and treated with 1 mg endo-β-N-acetylglucosaminidase for enzymatic digestion. The reaction mixture was mixed with water-soluble organic solvent thoroughly and centrifuged to collect the supernatant. The supernatant was purified by ion exchange column. 18 mg of glycan-101 ($Sia_2Gal_2GlcNAc_2Man_3GlcNAc$) was obtained.

A solution of glycan-101 ($Sia_2(\alpha2\text{-}6)$ $Gal_2GlcNAc_2Man_3GlcNAc$) (30 mg), 2-chloro-1,3-dimethylimidazolinium chloride (DMC) (62.7 mg) and $Et_3N$ (89 μL) in water was stirred at 4° C. for 1 h. The reaction mixture was subjected to gel filtration chromatography on a Sephadex G-25 column eluted by 0.05% aqueous $Et_3N$ to collect the glycan oxazoline-101.

Glycan oxazoline-101 was added to a mixture of endoglycosidase and anti-HER2 GAb201 in 50 mM Tris buffer (pH 7.8) and incubated for an hour at room temperature. The reaction mixture was purified with protein A affinity column, followed by amanion exchange column capto Q to collect the desired product, anti-HER2 GAb101. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb101.

Anti-HER2 GAb102

A solution of glycan-102 (Sia (α2-6) $Gal_2GlcNAc_2Man_3GlcNAc$) (30 mg), 2-chloro-1,3-dimethylimidazolinium chloride (DMC) (62.7 mg) and $Et_3N$ (89 μL) in water was stirred at 4° C. for 1 h. The reaction mixture was subjected to gel filtration chromatography on a Sephadex G-25 column and eluted by 0.05% aqueous Et3N. The fractions containing the product (glycan oxazoline-102) were combined and lyophilized to give a white powder.

Glycan oxazoline-102 was added to a mixture of endoglycosidase and anti-HER2 GAb201 in 50 mM Tris buffer (pH 7.8) and incubated for an hour at room temperature. The reaction mixture was purified with protein A affinity column, followed by amanion exchange column capto Q to collect the desired product, anti-HER2 GAb102. The product was trypsinized, and the glycopeptides, TKPREEQYNSTYR (SEQ ID NO: 3) and EEQYNSTYR (SEQ ID NO: 4) were analyzed using nanospray LC/MS to confirm the glycosylation pattern of anti-HER2 GAb102.

Anti-HER2 GAb103

A solution of glycan-103 (Sia($\alpha$2-6) GalGlcNAc$_2$Man$_3$GlcNAc) (30 mg), 2-chloro-1,3-dimethylimidazolinium chloride (DMC) (62.7 mg) and Et$_3$N (89 µL) in water (593 µL) was stirred at 4° C. for 1 h. The reaction mixture was subjected to gel filtration chromatography on a Sephadex G-25 column and eluted by 0.05% aqueous Et$_3$N. The fractions containing the product (glycan oxazoline-103) were combined and lyophilized to give a white powder.

Glycan oxazoline-103 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb103. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb103.

Anti-HER2 GAb104

A solution of glycan-104 (Gal$_2$GlcNAc$_2$Man$_3$GlcNAc) (30 mg), 2-chloro-1,3-dimethylimidazolinium chloride (DMC) (62.7 mg) and Et$_3$N (89 µL) in water was stirred at 4° C. for 1 h. The reaction mixture was subjected to gel filtration chromatography on a Sephadex G-25 column and eluted by 0.05% aqueous Et$_3$N. The fractions containing the product (glycan oxazoline-104) were combined and lyophilized to give a white powder.

Glycan oxazoline-104 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb104. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb104.

Anti-HER2 GAb 105

A solution of glycan-105 (GalGlcNAc$_2$Man$_3$GlcNAc) (30 mg), 2-chloro-1,3-dimethylimidazolinium chloride (DMC) (62.7 mg) and Et$_3$N (89 µL) in water was stirred at 4° C. for 1 h. The reaction mixture was subjected to gel filtration chromatography on a Sephadex G-25 column and eluted by 0.05% aqueous Et$_3$N. The fractions containing the product (glycan oxazoline-105) were combined and lyophilized to give a white powder.

Glycan oxazoline-105 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb105. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb105.

Anti-HER2 GAb 106

A solution of glycan-106 (GalGlcNAcMan$_3$GlcNAc) (30 mg), 2-chloro-1,3-dimethylimidazolinium chloride (DMC) (62.7 mg) and Et$_3$N (89 µL) in water (593 µL) was stirred at 4° C. for 1 h. The reaction mixture was subjected to gel filtration chromatography on a Sephadex G-25 column and eluted by 0.05% aqueous Et3N. The fractions containing the product (glycan oxazoline-106) were combined and lyophilized to give a white powder.

Glycan oxazoline-106 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb106. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb106.

Anti-HER2 GAb107

A solution of glycan-107 (GlcNAc$_3$Man$_3$GlcNAc) (30 mg), 2-chloro-1,3-dimethylimidazolinium chloride (DMC) (62.7 mg) and Et$_3$N (89 µL) in water was stirred at 4° C. for 1 h. The reaction mixture was subjected to gel filtration chromatography on a Sephadex G-25 column and eluted by 0.05% aqueous Et$_3$N. The fractions containing the product (glycan oxazoline-107) were combined and lyophilized to give a white powder.

Glycan oxazoline-107 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb107. The product was trypsinized, and the glycopeptides, TKPREEQYNSTYR (SEQ ID NO: 3) and EEQYN STYR (SEQ ID NO: 4), were analyzed using nanospray LC/MS to confirm the glycosylation pattern of anti-HER2 GAb107.

Anti-HER2 GAb 108

A solution of glycan-108 (GlcNAc$_2$Man$_3$GlcNAc) (30 mg), 2-chloro-1,3-dimethylimidazolinium chloride (DMC) (62.7 mg) and Et$_3$N (89 µL) in water was stirred at 4° C. for 1 h. The reaction mixture was subjected to gel filtration chromatography on a Sephadex G-25 column and eluted by 0.05% aqueous Et$_3$N. The fractions containing the product (glycan oxazoline-108) were combined and lyophilized to give a white powder.

Glycan oxazoline-108 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb108. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb108.

Anti-HER2 GAb109

A solution of glycan-109 (GlcNAcMan$_3$GlcNAc) (30 mg), 2-chloro-1,3-dimethylimidazolinium chloride (DMC) (62.7 mg) and Et$_3$N (89 µL) in water was stirred at 4° C. for 1 h. The reaction mixture was subjected to gel filtration chromatography on a Sephadex G-25 column and eluted by 0.05% aqueous Et$_3$N. The fractions containing the product (glycan oxazoline-109) were combined and lyophilized to give a white powder.

Glycan oxazoline-109 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb 109. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb109.

Anti-HER2 GAb110

A solution of glycan-110 (GlcNAcMan$_3$GlcNAc) (30 mg), 2-chloro-1,3-dimethylimidazolinium chloride (DMC) (62.7 mg) and Et$_3$N (89 µL) in water was stirred at 4° C. for 1 h. The reaction mixture was subjected to gel filtration chromatography on a Sephadex G-25 column and eluted by 0.05% aqueous Et$_3$N. The fractions containing the product (glycan oxazoline-110) were combined and lyophilized to give a white powder.

Glycan oxazoline-110 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb110. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb110.

Anti-HER2 GAb111

A solution of glycan-111 (Man$_3$GlcNAc) (30 mg), 2-chloro-1,3-dimethylimidazolinium chloride (DMC) (62.7 mg) and Et$_3$N (89 µL) in water was stirred at 4° C. for 1 h. The reaction mixture was subjected to gel filtration chromatography on a Sephadex G-25 column and eluted by 0.05% aqueous Et3N. The fractions containing the product (glycan oxazoline-111) were combined and lyophilized to give a white powder.

Glycan oxazoline-111 was added to a mixture of endoglycosidase and anti-HER2 GAb 201 in 50 mM Tris buffer (pH 7.8) and incubated for an hour at room temperature. The reaction mixture was purified with protein A affinity column, followed by amanion exchange column capto Q to collect the desired product, anti-HER2 GAb111. The product was trypsinized, and the glycopeptides, TKPREEQYNSTYR (SEQ ID NO: 3) and EEQYNSTYR (SEQ ID NO: 4), were analyzed using nanospray LC/MS to confirm the glycosylation pattern of anti-HER2 GAb111.

Example 2

Characterization of Anti-HER2 GAbs

General

MS spectrometry analysis of of glycoengineered mAb. Intact molecular weights of glycoengineered antibodies were detected by LC-ESI-MS on a LTQ Orbitrap XL ETD mass spectrometer (Thermo Fisher Scientific, San Jose, Calif.) equipped with ACQUITY UPLC (Waters, Milford, Mass.), using a BEH C4 column (1.0 mm×150 mm, 1.7 ☐m, Waters, Milford, Mass.). Briefly, the gradient employed was 1% buffer B at 3 min to 40% buffer B at 20 min with a flow rate of 50 uL/min, where buffer A was 0.1% formic acid in H$_2$O and buffer B was 0.1% formic acid in 80% acetonitrile. Full-scan MS condition: mass range m/z 800-4000 with Iontrap. Electrospray voltage was maintained at 4.0 kV and capillary temperature was set at 275° C.

For the analysis of trypsinized glycopeptides, high resolution and high mass accuracy nanoflow LC-MS/MS experiments were done on a LTQFT Ultra (Linear quadrupole ion trap Fourier transform ion cyclotron resonance) mass spectrometer (Thermo Electron, san Jose, Calif.) equipped with a nanoelectrospry ion source (New Objective, Inc.), an Agilent 1100 Series binary high-performance liquid chromatography pump (Agilent Technologies, Palo Alto, Calif.), and a Famos autosampler (LC Packings, San Francisco, Calif.). The disgestion solution was injected (6 µl) at 10 µl/min flow rate on to a self packed precolumn (150 µm I.D.×20 mm, 5 µm, 100 Å). Chromatographic separation was performed on a self packed reversed phase C18 nanocolumn (75 µm I.D.×300 mm, 5 µm, 100 Å) using 0.1% formic acid in water as mobile phase A and 0.1% formic acid in 80% acetonitrile as mobile phase B operated at 300 nl/min flow rate. Survey full-scan MS condition: mass range m/z 320-2000, resolution 100,000 at m/z 400. The ten most intense ions were sequentially isolated for MS2 by LTQ. Electrospray voltage was maintained at 1.8 kV and capillary temperature was set at 200° C.

Analysis of N-Glycosylation in Trastuzumab

We developed a mass spectrometric method to monitor the yield of oligosaccharide-derived fragment ions (oxonium ions) over a collision induced dissociation (CID) energy applied to a glycopeptides precursor. Multiple Reaction Monitoring (MRM) of oxonium ions method could fulfill the regulatory requirement on the routine quality control analysis of forthcoming biosimilar therapeutics.

5 µg of Trastuzumab was dissolved in 25 µL of 2M Guanidine-HCl, and dithiothreitol (DTT) were added to a final concentration of 5 mM. After 10 minutes incubation in 110° C., reduced cysteine residues were alkylated in 10 mM Iodoacetamide (IAA) at 37° C. for 1 hour. Add 5 mM DTT to quench excess IAA at RT for 10 minutes. The product was diluted 15 times in 50 mM ammonium bicarbonate before microcentrifugation with spin column (10 kDa protein MW cut-off). The trypsin digestion was performed for 4 hours at 37° C. using an enzyme: protein ratio of 1:25 (w/w). Sample was frozen at −20° C. for LC-MS/MS analysis.

The glycopeptide quantification by m/z 204 oxonium ion (HexNAc) monitoring was performed using a 4000 QTrap triple quadrupole mass spectrometer (AB Sciex) with Aglient 1200 HPLC system. For relative quantification of glycopeptide microheterogeneity, precursor ion m/z was derived in-silico, covering all possible glycan compositions, and a single quantitative transition was monitored for each precursor ion (Q3 m/z-=204).

MS Data Analysis

The acquired raw data was processed with Analyst 1.5 (AB Sciex). The mass chromatogram of each transition was integrated and quantified by peak area. The percentage composition of each component was calculated with respect to the sum of all components combined.

Figure 3:
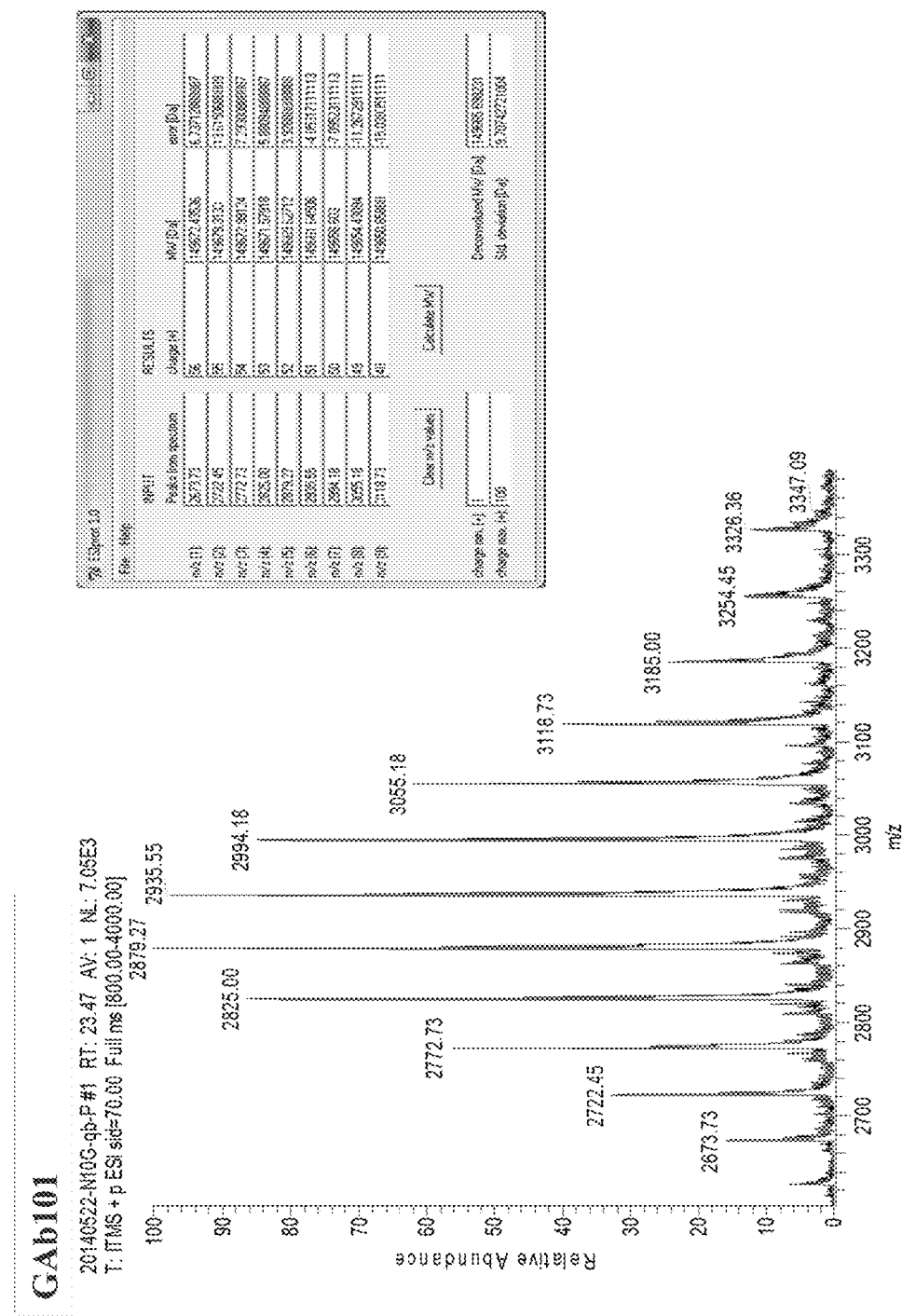
FIG. 3 shows the intact molecular weight of anti-HER2 GAb101 by ESI/MS.
Figure 4:
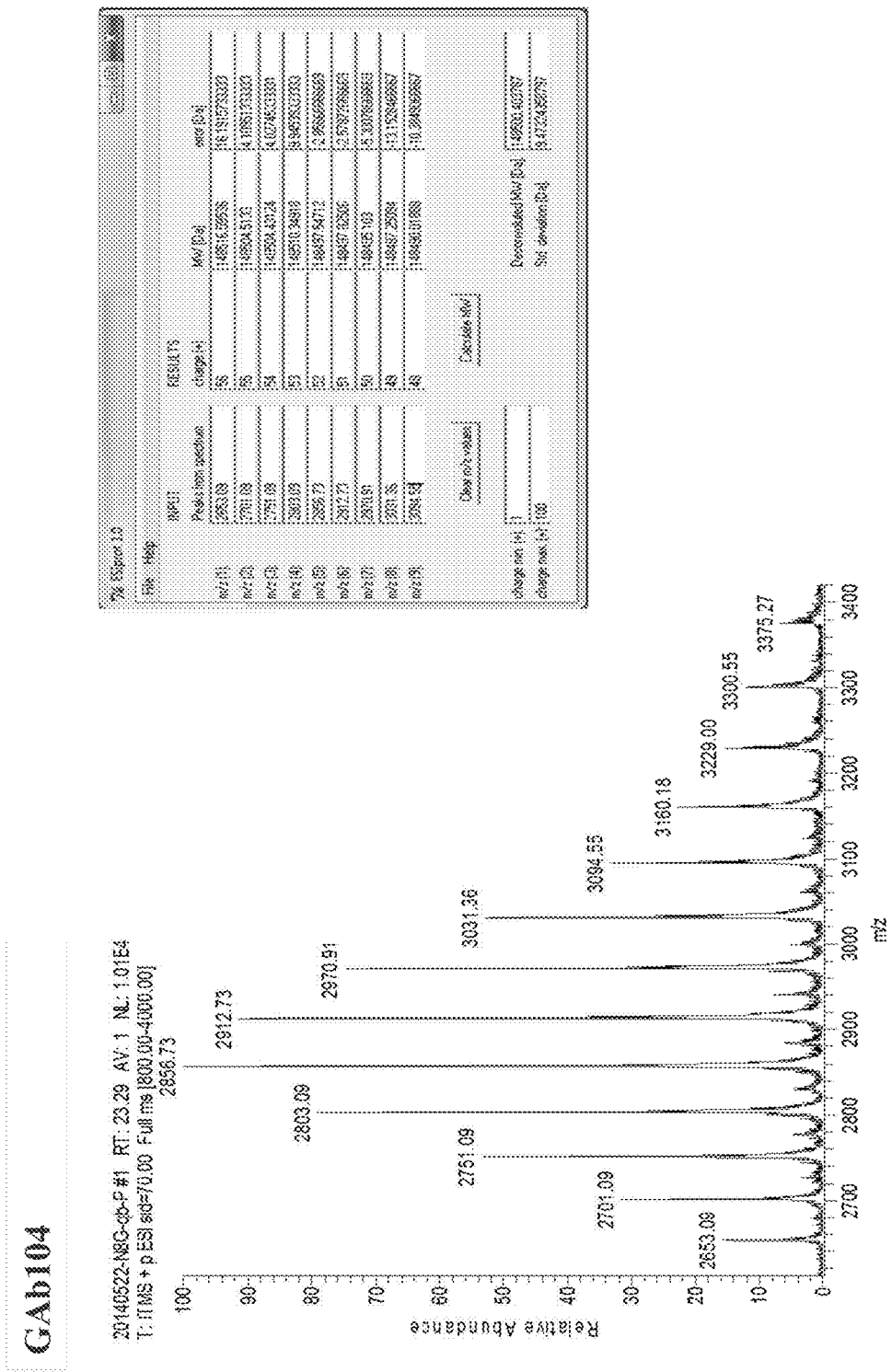
FIG. 4 shows the intact molecular weight of anti-HER2 GAb104 by ESI/MS.
Figure 5:
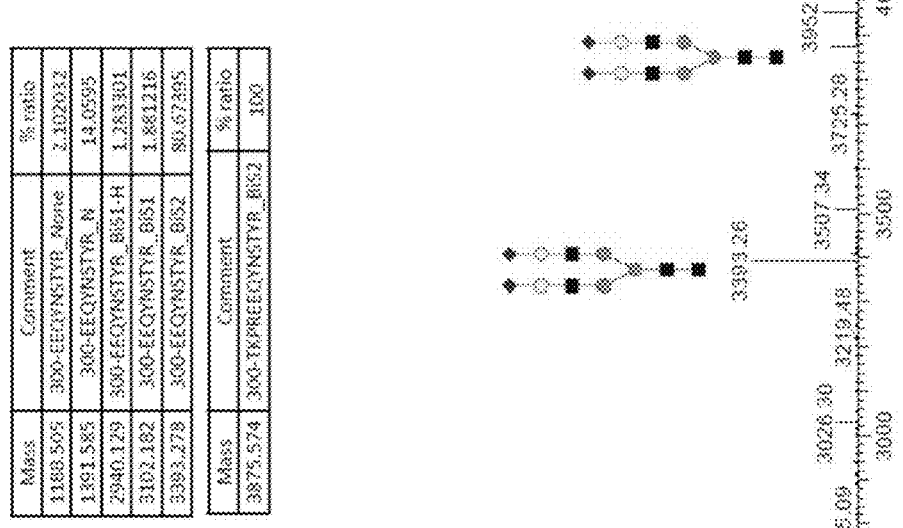
FIG. 5 shows the MS spectrum of the cleavaged glycopeptide TKPREEQYNSTYR (SEQ ID NO: 3) after trypsin digestion of anti-HER2 GAbs 101.
Figure 5:
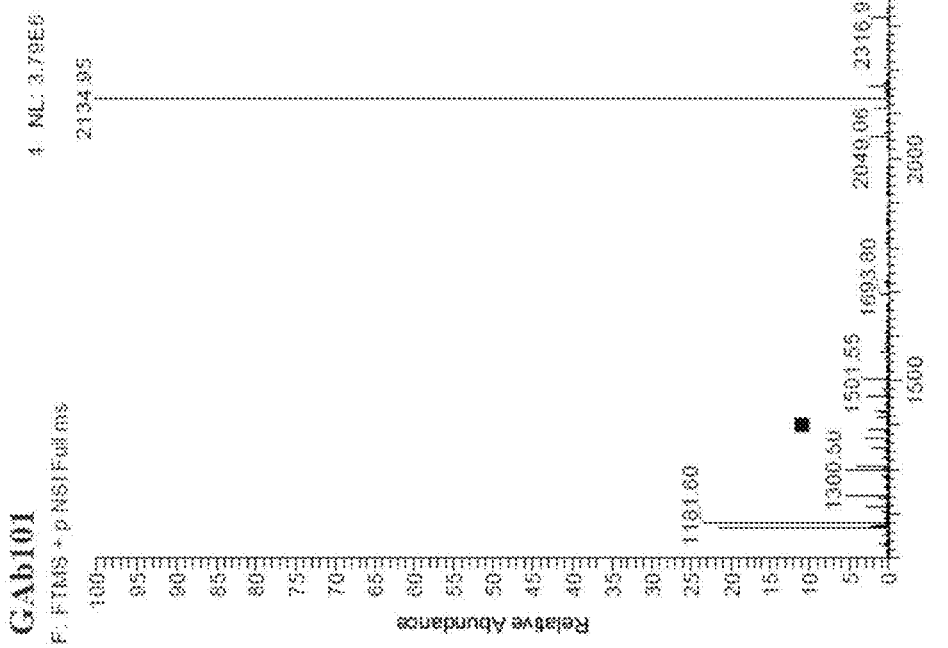
Figure 6:
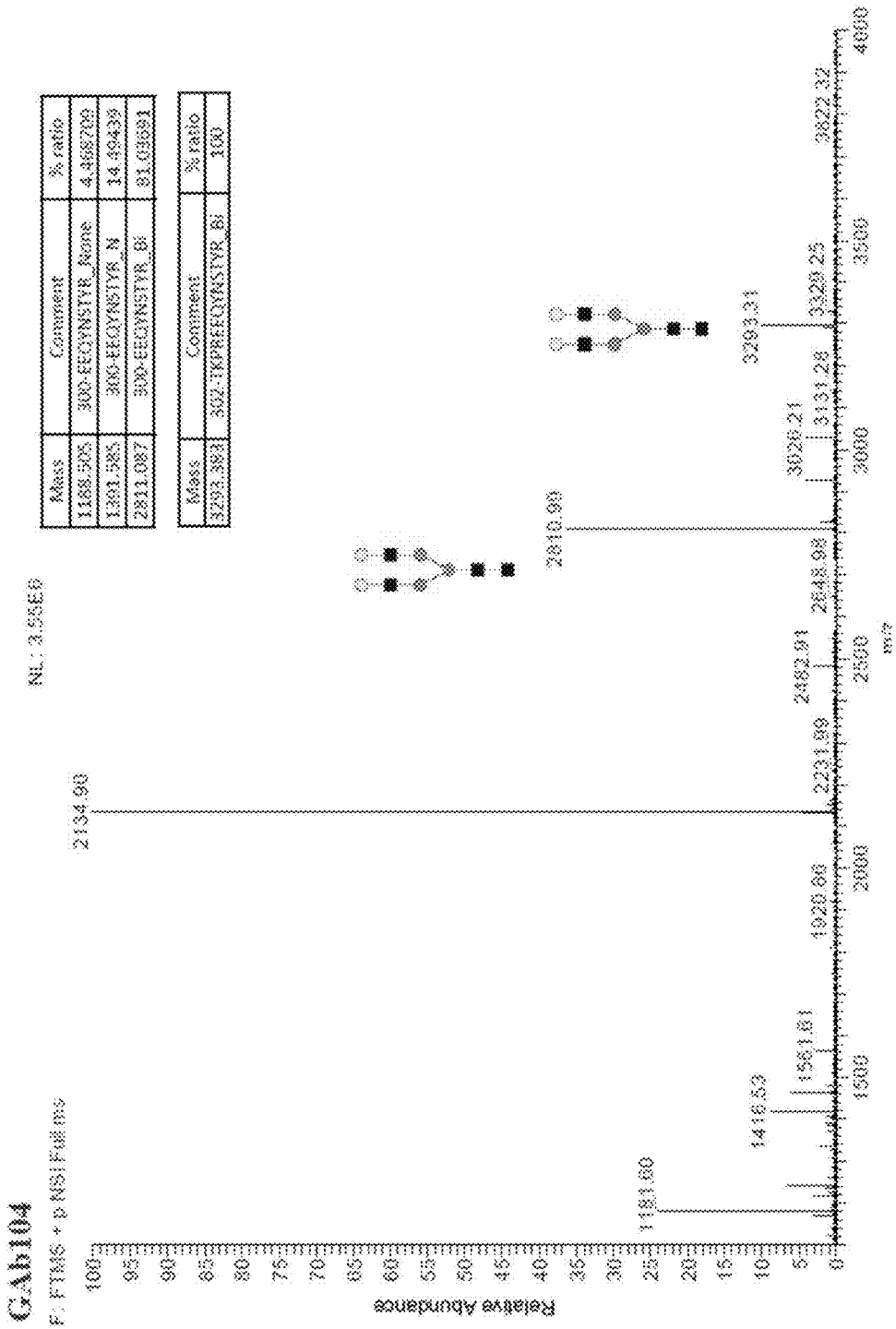
FIG. 6 shows MS spectrum of the cleavaged glycopeptide TKPREEQYNSTYR (SEQ ID NO: 3) after trypsin digestion of anti-HER2 GAbs 104.

Glycan oxazoline-101 was added to mixture of EndoS and anti-HER2 Gab201 in 50 mM Tris buffer (pH7.8) and incubated for 0.5-1 hr at r.t. or 30° C. After the reaction is completed, anti-HER2 Gab101 was purified with protein A affinity column and loaded to an anion exchange column capto Q for further purification. The purified anti-HER2 Gab101was confirmed by SDS-PAGE, and the molecular weight of the IgG molecule of anti-HER2 GAb101 was confirmed by MS (Table 6, FIGS. 3 and 4 for anti-HER2 GAbs 101 and 104). The N-glycan profiling was performed by trypsin digestion, and analyzed by nanospray LC/MS based on the cleavaged glycopeptide TKPREEQYNSTYR (SEQ ID NO: 3). Anti-HER2 GAbs 102, 104, 105, 106, 107, 108, 110 and 111 were synthesized in the same manner, and analyzed by the same procedures as described herein. Results of N-glycan profiling for anti-HER2 GAbs 101,102, 104, 105, 106, 107, 108, 110 and 111 are shown in Table 7. FIGS. 5 and 6 show the MS of the cleavaged glycopeptide TKPREEQYNSTYR (SEQ ID NO: 3) after trypsin digestion of anti-HER2 GAbs 101 and 104.

Table 6. ESI/MS analysis: Intact molecular weight of anti-HER2 Gabs

TABLE 6

| Anti-HER2 GAb | Apex | Delta Mass | Delta Mass/2 | Glycan Composition | Theroy Mass | Delta Ms (Da) |
|---|---|---|---|---|---|---|
| 200 | 145652.650453 | 0 | 0 | | | |
| 110 | 147443.710616 | 1791.06 | 895.5301 | +N2H3 | 893.32 | 2.2101 |
| 105 | 148181.406009 | 2528.756 | 1264.378 | +N3H4 | 1258.45 | 5.928 |
| 106 | 148175.984898 | 2523.334 | 1261.667 | +N3H4 | 1258.45 | 3.217 |
| 111 | 147037.808231 | 1385.158 | 692.5789 | +N1H3 | 690.24 | 2.3389 |
| 102 | 148760.418231 | 3107.768 | 1553.884 | +N3H4S1 | 1549.55 | 4.334 |
| 108 | 147843.822838 | 2191.172 | 1095.586 | +N3H3 | 1096.40 | −0.814 |
| 107 | 148258.908231 | 2606.258 | 1303.129 | +N4H3 | 1299.48 | 3.649 |
| 104 | 148500.403787 | 2847.753 | 1423.877 | +N3H5 | 1420.51 | 3.367 |
| 101 | 149665.698231 | 4013.048 | 2006.524 | +N3H5S2 | 2002.70 | 3.824 |

Table 7. N-glycan profiling of anti-HER2 Gabs

TABLE 7

| Anti-HER2 | Glycan oxazoline | Convergent yield by LC/MS analysis of TKPREEQYNSTYR | Yield |
|---|---|---|---|
| GAb110 | | 100% | 59.1% |
| GAb105 | | 100% | 63.3% |
| GAb106 | | 100% | 52.0% |
| GAb111 | | 96% | 77.4% |
| GAb102 | | 100% | 77.1% |
| GAb108 | | 100% | 80.6% |
| GAb107 | | 100% | 52.1% |

TABLE 7-continued

| Anti-HER2 | Glycan oxazoline | Convergent yield by LC/MS analysis of TKPREEQYNSTYR | Yield |
|---|---|---|---|
| GAb104 | (biantennary structure with 2β, 4β terminal residues) | 100% | 35.4% |
| GAb101 | (biantennary structure with 2β, 4β, 6α sialylated residues) | 100% | 56.2% |

Example 3

Anti-HER2 GAb ELISA Binding Assay

General

SDS-PAGE detection of glycoengineered Herceptin antibodies. All the SDS-PAGE analysis was performed with NuPAGE® Novex® 4-12% Bis-Tris gel (Invitrogen) ether with or without DTT addition.

Recombinant human HER2 protein (purchased from Sino Biological Inc.) (1 μg/mL) in 100 μL carbonate coating buffer (pH 10) was coated onto 96 well high binding plates at 4° C. for overnight. 2% of bovine serum albumin in PBST was then added to block plates at r.t. for 1 hr and subsequently a series dilution of anti-HER2 GAbs 101, 102, 104, 105, 106, 107, 108, 110 and 111 were added to plates and incubated for one hour. After incubation, HRP conjugated anti-human IgG was added to the reaction mixture and incubated for one hour. An aliquot of OPD substrate was added, and the absorbance at 450 nm was recorded. Throughout the experiment, plates were washed with PBS twice after each incubation step. Results of ELISA binding are shown in Table 8.

TABLE 8

ELISA Binding

Anti-Her2 binding assay

| | Herceptin | GAb108 | GAb107 | GAb104 | GAb106 | GAb102 | Herceptin-GlcNAc | Rituximab |
|---|---|---|---|---|---|---|---|---|
| One site--Specific binding | | | | | | | | |
| Best-fit values Bmax | 2.132 | 2.112 | 2.115 | 2.157 | 2.178 | 2.184 | 2.207 | 0.06371 |
| kd(nM) | 0.07866 | 0.1211 | 0.1253 | 0.1314 | 0.1133 | 0.1166 | 0.1136 | 7.649e−006 |
| Std. Error Bmax | 0.01943 | 0.03244 | 0.02712 | 0.02649 | 0.03114 | 0.03384 | 0.03343 | 0.01146 |
| Kd | 0.003587 | 0.008818 | 0.007584 | 0.007571 | 0.007750 | 0.008611 | 0.008225 | 0.0007792 |
| 95% Confidence Intervals | | | | | | | | |
| Bmax | 2.090 to 2.174 | 2.043 to 2.182 | 2.057 to 2.173 | 2.100 to 2.214 | 2.102 to 2.254 | 2.101 to 2.266 | 2.125 to 2.289 | 0.03566 to 0.09176 |
| Kd | 0.07096 to 0.08635 | 0.1022 to 0.1400 | 0.1091 to 0.1416 | 0.1152 to 0.1477 | 0.09437 to 0.1323 | 0.09554 to 0.1337 | 0.09346 to 0.1337 | −0.001899 to 0.001914 |
| Goodness of Fit | | | | | | | | |
| Degrees of Freedom | 14 | 14 | 14 | 14 | 6 | 6 | 6 | 6 |
| R2 | 0.9981 | 0.9954 | 0.9968 | 0.9971 | 0.9982 | 0.9980 | 0.9980 | −101.1 |
| Absolute Sum of Squares | 0.02061 | 0.04883 | 0.03363 | 0.03146 | 0.009902 | 0.01156 | 0.01140 | 0.004201 |
| Sy.x | 0.03837 | 0.05906 | 0.04901 | 0.04741 | 0.04062 | 0.04389 | 0.04358 | 0.02646 |
| Number of points Analyzed | 16 | 16 | 16 | 16 | 8 | 8 | 8 | 8 |

Example 4

ADCC Reporter Bioassay of Anti-HER2 GAbs in SK-BR-3 Cells

ADCC assay was performed with Promega reporter bioassay kit. Target cell, SK-BR-3 cancer cell line was obtained from ATCC and maintained in McCoy's 5A (modified) medium (Gibco) supplemented with 10% heat-inactivated fetal bovine serum and 1% Antibiotic-Antimycotic (Gibco).

Figure 7:
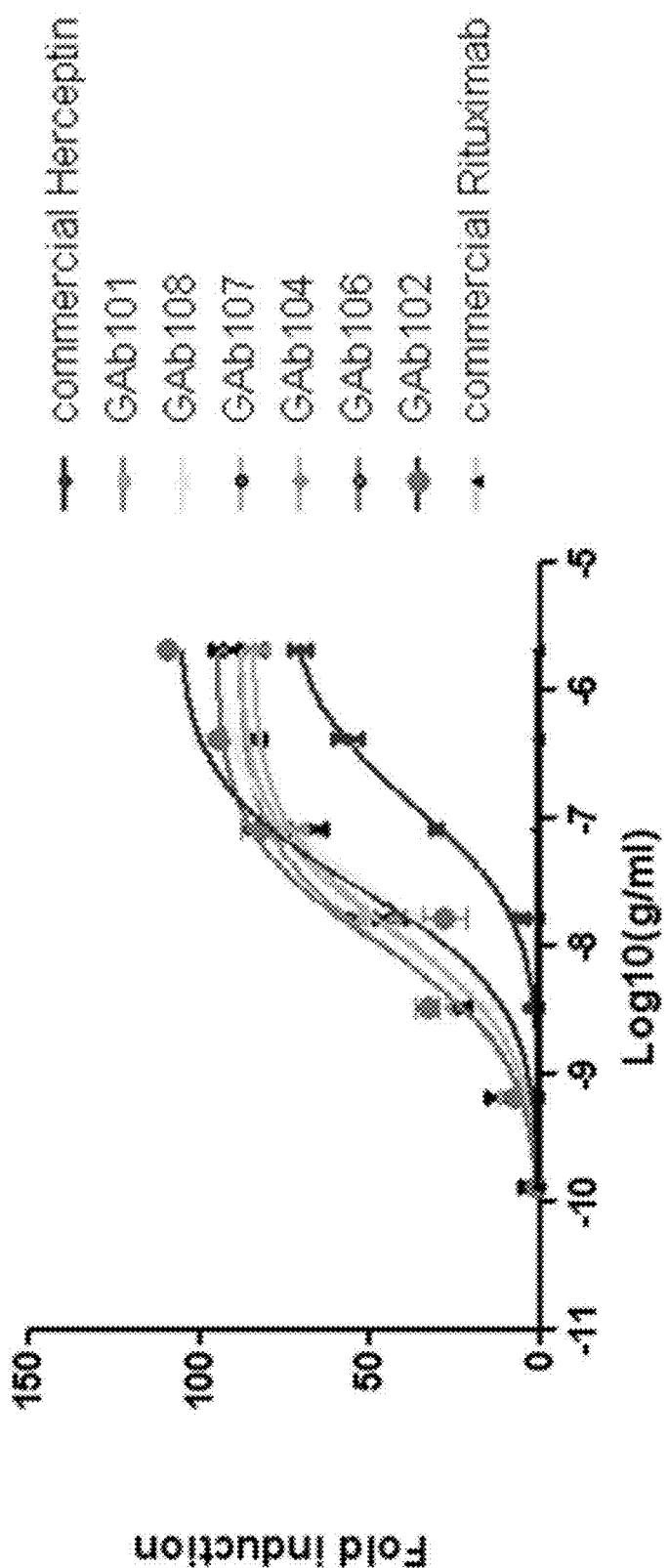
FIG. 7 shows ADCC activities of anti-HER2 GAbs 101, 102, 104, 106, 107, 108, and Trastuzumab. Rituximab was used as a negative control.

When ready for ADCC assay, SK-BR-3 cells were harvested and plated in 384 well microplates for 2 days. Then, series titration of Herceptin with different glycan forms were added and followed by incubation with NFAT engineered Jurkat cells expressing FcγIIIa receptor with V158 variant for 6 hrs at 37° C. The readout was done through adding Bio-Glow luciferase substrate to plates and recorded with victor3 luminescence plate reader. The ratio of effector cell to target cell is 12.5. Results are shown in FIG. 7 and Table 9.

TABLE 9 lists ADCC activities of anti-HER2 GAbs and Trastuzumab.

| Anti-HER2 | Trastuzumab | GAb101 | GAb104 | GAb105 | GAb107 | GAb108 | GAb111 |
|---|---|---|---|---|---|---|---|
| ADCC (fold) | 1 | 30 | 14.3 | 9.5 | 10 | 6.5 | 3 |

Example 5

Binding Affinity of Anti-HER2 GAbs to FcγRIIIA

General

Surface Plasmon Resonance (SPR) Analysis.

All the SPR experiments were performed with BIACORE T200 at 25° C. using HBS-EP (10 mM HEPES pH7.4, 0.15M NaCl, 3 mM EDTA, 0.005% surfactant P20) as running buffer. The (Fab')$_2$ fragment of goat anti-human (Fab')$_2$ (Jackson Immuno Research Inc.) was utilized to capture antibody samples after immobilized onto both the reference and active channels of CM5 sensor chip. Interactions between glycoengineered antibodies and complex-type glycosylated FcγRIIIA (expressed from HEK293 cells) were recorded through single cycle kinetic methods using five different concentrations of FcγRIIIA at 30 ul/min for association with 240 seconds followed by dissociation time of 420 seconds. Data was processed with double-referencing for background subtraction and fitted to 1:1 Langmuir binding model in BiaEvaluation software (GE Healthcare) to get kinetic/affinity constants.

FcγRIIIA was transfected into HEK-293 cell line to express recombinant protein. The secreted FcγRIIIA recombinant protein was purified and then diluted to serial concentration in HBS-EP buffer (200 nM, 100 nM, 50 nM, 25 nM, and 12.5 nM). Each of anti-HER2 GAb101, GAb102, GAb103, GAb104, GAb105, GAb106, GAb107, GAb108, GAb109, GAb110 and GAb111 was diluted in HBS-EP buffer to the concentration of 10 mg/ml, and then captured to the CM5 chip in which anti-human Fab domain antibodies were pre-immobilized. A serial titration of FcγRIIIA was injected and bound at the flow rate of 30 ml/min. Single cycle kinetics data was fitted into 1:1 binding model using Biacore T200 evaluation software to measure the equilibrium constant (Ka/Kd). The results were shown in Table 4.

We claim:

1. A composition of anti-HER2 glycoantibodies or antigen binding fragments comprising a homogeneous population of glycoengineered anti-HER2 IgG antibodies having the same N-glycan at the Asn-297 position in the Fc region of each anti-HER2 IgG antibody, wherein the N-glycan is selected from the group consisting of $Sia_2(\alpha 2\text{-}6)Gal_2GlcNAc_2Man_3GlcNAc_2$,
$Gal_2GlcNAc_2Man_3GlcNAc_2$, $Sia_2(\alpha 2\text{-}6)$
$Gal_2GlcNAc_2Man_3GlcNAc_2$, $Sia_2(\alpha 2\text{-}3)$
$Gal_2GlcNAc_3Man_3GlcNAc_2$, $Sia_2(\alpha 2\text{-}3/\alpha 2\text{-}6)$
$Gal_2GlcNAc_2Man_3GlcNAc_2$, $Sia_2(\alpha 2\text{-}6/\alpha 2\text{-}3)$
$Gal_2GlcNAc_2Man_3GlcNAc_2$, $Sia_2(\alpha 2\text{-}3/\alpha 2\text{-}6)$
$Gal_2GlcNAc_3Man_3GlcNAc_2$, $Sia_2(\alpha 2\text{-}6/\alpha 2\text{-}3)$
$Gal_2GlcNAc_3Man_3GlcNAc_2$, $Sia(\alpha 2\text{-}6)$
$Gal_2GlcNAc_2Man_3GlcNAc_2$, $Sia(\alpha 2\text{-}3)$
$Gal_2GlcNAc_2Man_3GlcNAc_2$, $Sia(\alpha 2\text{-}6)$
$Gal_2GlcNAc_3Man_3GlcNAc_2$, $Sia(\alpha 2\text{-}3)$
$Gal_2GlcNAc_3Man_3GlcNAc_2$, $Sia(\alpha 2\text{-}6)$
$Gal_2GlcNAc_3Man_3GlcNAc_2$, $Sia(\alpha 2\text{-}3)$
$GalGlcNAc_2Man_3GlcNAc_2$, $Sia(\alpha 2\text{-}3)$
$GalGlcNAc_2Man_3GlcNAc_2$, $Sia(\alpha 2\text{-}6)$
$GalGlcNAc_3Man_3GlcNAc_2$, $Sia(\alpha 2\text{-}3)$
$GalGlcNAc_3Man_3GlcNAc_2$,
$Gal_2GlcNAc_2Man_3GlcNAc_2$,
$Gal_2GlcNAc_3Man_3GlcNAc_2$,
$GalGlcNAc_2Man_3GlcNAc_2$,
$GalGlcNAc_3Man_3GlcNAc_2$, $GlcNAc_3Man_3GlcNAc_2$,
$GlcNAc_2$, Man3GlcNAc$_2$, GlcNAcMan$_3$GlcNAc$_2$ and
$Man_3GlcNAc_2$.

2. The composition of claim 1, wherein the glycoengineered anti-HER2 IgG antibody comprises a heavy chain having the amino acid sequence set forth in SEQ ID NO: 1, and a light chain having the amino acid sequence set forth in SEQ ID NO: 2.

3. The composition of claim 1, wherein the glycoengineered anti-HER2 IgG antibody comprises a light chain sequence and a heavy chain sequence of Trastuzumab (Herceptin).

4. The composition of claim 1, wherein the N-glycan is selected from the group consisting of $Sia_2(\alpha 2\text{-}6)$ $Gal_2GlcNAc_2Man_3GlcNAc_2$, $Gal_2GlcNAc_2Man_3GlcNAc_2$, $GalGlcNAc_2Man_3GlcNAc_2$, $GlcN\text{-}Ac_2Man_3GlcNAc_2$, $GlcNAc_2Man_3GlcNAc_2$, and $Man_3GlcNAc_2$, and wherein the anti-HER2 glycoantibodies have improved ADCC over Trastuzumab.

5. The composition of claim 1, wherein the N-glycan is selected from the group consisting of $Sia_2(\alpha 2\text{-}6)$ Gal$_2$GlcNAc$_2$Man$_3$GlcNAc$_2$, Sia$_2$(α2-3) Gal$_2$GlcNAc$_2$Man$_3$GlcNAc$_2$, Sia(α2-6) GalGlcNAc$_2$Man$_3$GlcNAc$_2$, Gal$_2$GlcNAc$_2$Man$_3$GlcNAc$_2$, GalGlcNAc$_2$Man$_3$GlcNAc$_2$, GalGlcNAcMan$_3$GlcNAc$_2$, GlcNAc$_3$Man$_3$GlcNAc$_2$, GlcNAc$_2$Man$_3$GlcNAc$_2$, GlcNAcMan$_3$GlcNAc$_2$ and Man$_3$GlcNAc$_2$, and wherein the anti-HER2 glycoantibodies have improved binding to FcγRIIIA over Trastuzumab.

6. The composition of claim 1, wherein the N-glycan is free of fucose.

7. The composition of claim 1, wherein the N-glycan is selected from the group consisting of Sia$_2$(α2-6) Gal$_2$GlcNAc$_2$Man$_3$GlcNAc$_2$, Sia$_2$(α2-3) Gal$_2$GlcNAc$_2$Man$_3$GlcNAc$_2$, Sia(α2-6) GalGlcNAc$_2$Man$_3$GlcNAc$_2$, Gal$_2$GlcNAc$_2$Man$_3$GlcNAc$_2$, GalGlcNAc$_2$Man$_3$GlcNAc$_2$, GlcNAc$_3$Man$_3$GlcNAc$_2$, GlcNAc$_2$Man$_3$GlcNAc$_2$, GlcNAcMan$_3$GlcNAc$_2$ and Man$_3$GlcNAc$_2$.

8. The composition of claim 1, wherein the N-glycan is selected from the group consisting of Sia$_2$(α2-3) Gal$_2$GlcNAc$_2$Man$_3$GlcNAc$_2$, Gal$_2$GlcNAc$_2$Man$_3$GlcNAc$_2$, GlcNAc$_3$Man$_3$GlcNAc$_2$, GlcNAcMan$_3$GlcNAc$_2$, Man$_3$GlcNAc$_2$, and GalGlcNAc$_2$Man$_3$GlcNAc$_2$.

9. The composition of claim 1, wherein the glycoengineered anti-HER2 IgG antibody has the N-glycan GlcNAcMan$_3$GlcNAc$_2$ having the glycan structure shown for GAb 109 depicted in Table 2:

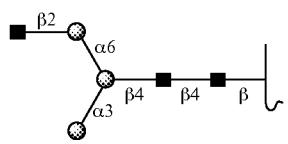

wherein ■ is an N-acetylglucosamine (GlcNAc) and ● is a mannose (Man).

10. The composition of claim 1, wherein the glycoengineered anti-HER2 IgG molecule antibody has the N-glycan GlcNAcMan$_3$GlcNAc$_2$ having the glycan structure shown for GAb 110 depicted in Table 2:

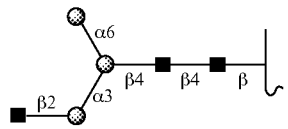

wherein ■ is an N-acetylglucosamine (GlcNAc) and ● is a mannose (Man).

11. A pharmaceutical formulation comprising a composition of anti-HER2 glycoantibodies or antigen binding fragments according to claim 1 and a pharmaceutically acceptable carrier.

* * * * *

SEQUENCE LISTING

<160> NUMBER OF SEQ ID NOS: 6

<210> SEQ ID NO 1
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Thr Lys Pro Arg Glu Glu Gln Tyr Asn Ser Thr Tyr Arg
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Glu Gln Tyr Asn Ser Thr Tyr Arg
1               5

<210> SEQ ID NO 5
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Gln Lys Tyr Gln Pro Thr Glu Ala Asn Leu Lys Ala Arg Ser Glu
1               5                   10                  15

Phe Gln Asp Asn Lys Phe Gly Ile Phe Leu His Trp Gly Leu Tyr Ala
                20                  25                  30

Met Leu Ala Thr Gly Glu Trp Thr Met Thr Asn Asn Asn Leu Asn Tyr
            35                  40                  45

Lys Glu Tyr Ala Lys Leu Ala Gly Gly Phe Tyr Pro Ser Lys Phe Asp
        50                  55                  60

Ala Asp Lys Trp Val Ala Ala Ile Lys Ala Ser Gly Ala Lys Tyr Ile
65                  70                  75                  80

Cys Phe Thr Thr Arg His His Glu Gly Phe Ser Met Phe Asp Thr Lys
                85                  90                  95

Tyr Ser Asp Tyr Asn Ile Val Lys Ala Thr Pro Phe Lys Arg Asp Val
                100                 105                 110

Val Lys Glu Leu Ala Asp Ala Cys Ala Lys His Gly Ile Lys Leu His
            115                 120                 125

Phe Tyr Tyr Ser His Ile Asp Trp Tyr Arg Glu Asp Ala Pro Gln Gly
        130                 135                 140

Arg Thr Gly Arg Thr Gly Arg Pro Asn Pro Lys Gly Asp Trp Lys
145                 150                 155                 160

Ser Tyr Tyr Gln Phe Met Asn Asn Gln Leu Thr Glu Leu Leu Thr Asn
                165                 170                 175

Tyr Gly Pro Ile Gly Ala Ile Trp Phe Asp Gly Trp Asp Gln Asp
                180                 185                 190

Ile Asn Pro Asp Phe Asp Trp Glu Leu Pro Glu Gln Tyr Ala Leu Ile
            195                 200                 205

His Arg Leu Gln Pro Ala Cys Leu Val Gly Asn Asn His His Gln Thr
        210                 215                 220

Pro Phe Ala Gly Glu Asp Ile Gln Ile Phe Glu Arg Asp Leu Pro Gly
225                 230                 235                 240
```

-continued

```
Glu Asn Thr Ala Gly Leu Ser Gly Gln Ser Val Ser His Leu Pro Leu
                245                 250                 255

Glu Thr Cys Glu Thr Met Asn Gly Met Trp Gly Tyr Lys Ile Thr Asp
            260                 265                 270

Gln Asn Tyr Lys Ser Thr Lys Thr Leu Ile His Tyr Leu Val Lys Ala
            275                 280                 285

Ala Gly Lys Asp Ala Asn Leu Leu Met Asn Ile Gly Pro Gln Pro Asp
        290                 295                 300

Gly Glu Leu Pro Glu Val Ala Val Gln Arg Leu Lys Glu Val Gly Glu
305                 310                 315                 320

Trp Met Ser Lys Tyr Gly Glu Thr Ile Tyr Gly Thr Arg Gly Gly Leu
                325                 330                 335

Val Ala Pro His Asp Trp Gly Val Thr Thr Gln Lys Gly Asn Lys Leu
                340                 345                 350

Tyr Val His Ile Leu Asn Leu Gln Asp Lys Ala Leu Phe Leu Pro Ile
                355                 360                 365

Val Asp Lys Lys Val Lys Lys Ala Val Val Phe Ala Asp Lys Thr Pro
            370                 375                 380

Val Arg Phe Thr Lys Asn Lys Glu Gly Ile Val Leu Glu Leu Ala Lys
385                 390                 395                 400

Val Pro Thr Asp Val Asp Tyr Val Val Glu Leu Thr Ile Asp
                405                 410
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
<220> FEATURE:
<223> OTHER INFORMATION: See specification as filed for detailed
      description of substitutions and preferred embodiments

<400> SEQUENCE: 6

His His His His His His
1               5